US008428969B2

(12) United States Patent
Hahn et al.

(10) Patent No.: US 8,428,969 B2
(45) Date of Patent: Apr. 23, 2013

(54) SYSTEM AND METHOD FOR TRACKING MEDICAL IMAGING QUALITY

(75) Inventors: Jerad J. Hahn, Orono, MN (US); Ryan M. Krocak, Albertville, MN (US)

(73) Assignee: Atirix Medical Systems, Inc., Minneapolis, MN (US)

(*) Notice: Subject to any disclaimer, the term of this patent is extended or adjusted under 35 U.S.C. 154(b) by 1497 days.

(21) Appl. No.: 11/335,858

(22) Filed: Jan. 19, 2006

(65) Prior Publication Data

US 2006/0212317 A1    Sep. 21, 2006

Related U.S. Application Data

(60) Provisional application No. 60/742,668, filed on Dec. 6, 2005, provisional application No. 60/613,054, filed on Jan. 19, 2005.

(51) Int. Cl.
*G06F 19/00*    (2006.01)

(52) U.S. Cl.
USPC ............................................................ 705/3

(58) Field of Classification Search .................. 705/2, 3; 600/300; 601/2; 378/207; 383/128; 707/805; 382/128
See application file for complete search history.

(56) References Cited

U.S. PATENT DOCUMENTS

| | | | |
|---|---|---|---|
| 3,680,084 A * | 7/1972 | Franklin et al. .......... 340/815.47 |
| 5,235,510 A | 8/1993 | Yamada et al. | |
| 5,301,105 A | 4/1994 | Cummings, Jr. | |
| 5,469,353 A | 11/1995 | Pinskey et al. | |
| 5,513,101 A | 4/1996 | Pinsky et al. | |
| 5,655,084 A | 8/1997 | Pinsky et al. | |
| 5,748,907 A | 5/1998 | Crane | |
| 5,786,994 A * | 7/1998 | Friz et al. ......................... 700/79 |
| 5,841,835 A * | 11/1998 | Aufrichtig et al. ............. 378/207 |
| 6,006,191 A | 12/1999 | DiRienzo | |
| 6,115,489 A * | 9/2000 | Gupta et al. .................. 382/141 |
| 6,249,809 B1 | 6/2001 | Bro | |

(Continued)

OTHER PUBLICATIONS

Jacquelyn P. Hogge, MD, Carolyn H. Palmer, RTR(M), Caroline C. Muller, RTR(M), Sherrill T. Little, MD, Deborah C. Smith, RTR(M), Panos P. Fatouros, Phd, Ellen Shaw de Paredes, MD, Department of Radiology, Medical College of Virginia Commonwealt ; Quality Assurance in Mammography: Artifact Analysis; Mar. 1999; Radiographics, 19, 503-522; pp. 1-22.*

(Continued)

*Primary Examiner* — Gerald J. O'Connor
*Assistant Examiner* — Teresa Woods
(74) *Attorney, Agent, or Firm* — Dardi & Herbert, PLLC; Peter S. Dardi

(57) ABSTRACT

The mammography management system can provide for quality control of devices associated with the system. A method is provided for monitoring the quality standards of a mammography facility. The method can comprise generating a report that analyzes information collected in preselected data fields on the performance of a resource after automatically executing a quality control test plan configured for the resource at a preselected time. The quality control test plan is configured based on resource type.

A method can provide for monitoring the quality of exams performed on a plurality of patients. The method comprises generating a report automatically analyzing and organizing information collected on the accuracy of exams preformed on the plurality of the patients into statistics. These statistics can compare the information based on a radiologist or a facility with other radiologists other facilities or overall statistics for a plurality of radiologists or a plurality of facilities.

17 Claims, 34 Drawing Sheets

U.S. PATENT DOCUMENTS

| | | | |
|---|---|---|---|
| 6,272,469 B1 * | 8/2001 | Koritzinsky et al. | 705/2 |
| 6,370,480 B1 | 4/2002 | Gupta et al. | |
| 6,385,589 B1 | 5/2002 | Trusheim et al. | |
| 6,516,324 B1 * | 2/2003 | Jones et al. | 707/805 |
| 6,574,629 B1 * | 6/2003 | Cooke et al. | 707/10 |
| 6,891,920 B1 | 5/2005 | Minyard et al. | |
| 6,934,590 B2 | 8/2005 | Ogawa | |
| 7,039,723 B2 | 5/2006 | Hu et al. | |
| 7,072,931 B2 | 7/2006 | Goldhaber et al. | |
| 7,080,025 B2 | 7/2006 | Mifune et al. | |
| 7,189,000 B2 * | 3/2007 | Miyauchi et al. | 378/207 |
| 7,289,825 B2 * | 10/2007 | Fors et al. | 455/556.1 |
| 7,298,876 B1 * | 11/2007 | Marshall et al. | 382/128 |
| 2002/0131625 A1 * | 9/2002 | Vining et al. | 382/128 |
| 2003/0036683 A1 * | 2/2003 | Kehr et al. | 600/300 |
| 2003/0212580 A1 * | 11/2003 | Shen | 705/2 |
| 2004/0225531 A1 | 11/2004 | Serrano et al. | |
| 2004/0258291 A1 | 12/2004 | Gustafson | |
| 2005/0020945 A1 * | 1/2005 | Tosaya et al. | 601/2 |
| 2005/0203775 A1 | 9/2005 | Chesbrough | |
| 2005/0256743 A1 * | 11/2005 | Dale | 705/2 |
| 2006/0173663 A1 * | 8/2006 | Langheier et al. | 703/11 |
| 2006/0265295 A1 * | 11/2006 | Feanny | 705/32 |
| 2006/0274145 A1 | 12/2006 | Reiner | |
| 2007/0011024 A1 * | 1/2007 | Dale et al. | 705/2 |

OTHER PUBLICATIONS

Berns, "QC for FFDM: What You Must Do and What Really Matters," Northwestern University Medical School, Lynn Sage Comprehensive Breast Center (2000), pp. 1-28.

General Electric Medical Systems, "TiP-TV, Program Supplement, XR Mammography: Full Field Digital Mammography Quality Control, Part 1," (2003), pp. 1-28.

Peter et al., "Soft-Copy Quality Control of Digital Spot Images Obtained by Using X-ray Image Intensifiers," Medical Physics, Radiology 2000, vol. 216, No. 3 (2000), pp. 810-819.

* cited by examiner

```
MOM - Create Appointment - Microsoft Internal Explorer          _ □ ×
┌─────────────────────────────────────────────────────────────────┐
│ Create Appointment                                              │
│ Wednesday, December 12 2004, 9:00 AM                            │
│ Goodhealth Clinic - St. Paul, MN                                │
├─────────────────────────────────────────────────────────────────┤
│  Save and Close | Reschedule Appointment | ⊗ Cancel Appointment Creation │
│       Facility: Goodhealth Clinic - St. Paul, MN                │
│      Resource: Room 101                                         │
│    *Study Type: [-Please Select-  ▼]    *Breasts: ○ Unilateral ○ Bilateral │
│ Appointment Date: 12/12/2004 9:00 AM    *Length: [  ▼]   Arrival Time: 8:50 AM │
│       *Patient: [            ] 🔍      *DOB: [       ]   MRN: [       ] │
│    *Home Phone: [            ]          Work Phone: [       ]   │
│   *Referring Phy: [            ]  🔍 Referring Phy Office Phones: [  ] │
│         *Notes: [                                       ]       │
│                 [                                       ]       │
└─────────────────────────────────────────────────────────────────┘
```

```
MOM - View Appointment - Microsoft Internal Explorer            _ □ ×
┌─────────────────────────────────────────────────────────────────┐
│ Samantha Peterson                                               │
│ Wednesday, December 12 2004, 9:00 AM                            │
│ Goodhealth Clinic - St. Paul, MN                                │
├─────────────────────────────────────────────────────────────────┤
│ ✎ Modify  ✓Confirm  ⏱Arrive ⊚No Show | Reschedule |✗Cancel Appointment|⊗ Close Window │
│         Status: Schedule                                        │
│        Patient: Peterson, Samantha 📧 ✎   DOB: 12-14-1965  MRN: 324234 │
│    Home Phone: 651-555-1234                Work Phone: 651-555-9909 │
│   Referring Phy: Jones, Philip 📧 ✎        Referring Phy Office Phone: 612-555-3443 │
│ Appointment Date: 12/12/2004 9:00 AM - 10:00 AM  Length: 60   Arrival Time: 8:50 AM │
│       Facility: Goodhealth Clinic - St. Paul, MN              Actual Arrival Time: │
│      Resource: Room 101                                         │
│     Study Type: Mammogram - Bilateral                           │
│    Radiologists: Smith, Janet                                   │
│      Complaint: Description of the patient's reason for the exam. │
│     Audit Trail: Schedule         12/01/2004 10:32 AM  Robins, Jannet │
└─────────────────────────────────────────────────────────────────┘
```

MOM Mammography Operational Management

Janet Smith | GoodHealth Clinic - Roseville, Mn ▼ | My Account | Logout | Help | About                       03-25-2005

Exams 🔍 Exam Search | ▦ Exam Worklist | ▦ Compare/Repeat List | ▦ Final Outcome List | ▦ Lost to follow up List

Exams Awaiting Final Outcome

The following callback exams conducted at your facility are awaiting final diagnostic or pathology reports.

Display: ○ Priority Only ◉ All final Outcome Exams ○ Screening Exams ○ Diagnostic Exams ○ Procedure Exams

| Facility | Patient Name | MRN | Exam Type | Creation Data | Exam Status | |
|---|---|---|---|---|---|---|
| GoodHealth Clinic | Smith, Amy | 34544344 | Screening | 06-13-2004 | Callback | Final Outcome — 2310 |
| GoodHealth Clinic | Smith, Sharon | 34532444 | Screening | 06-13-2004 | Callback | Final Outcome — 2310 |
| GoodHealth Clinic | Smith, Jill | 23543434 | Diagnostic | 06-14-2004 | Callback | Final Outcome — 2310 |
| United Hospital | Anderson, Jenny | 34512223 | Procedure | 06-13-2004 | Pending Surgical Pathology | Final Outcome — 2310 |
| United Hospital | Wilson, Joan | 23532323 | Screening | 06-14-2004 | Pending Surgical | Final Outcome — 2310 |

< Previous 1 [2] 3 Next >

Sidebar: Facility Dashboard; Exams; Search; Create; Arrived Patients; Exam Worklist; Screening Worklist; Diagnostic Worklist; Procedure Worklist; Callback List; Compare/Repeat List; Lost to Follow-up List

Add Lesion
*Mark area of abnormality on the diagram.
Calc=Calcifications  Mass=Mass  AD=Asymeteric Density  Arch=Architectual Distortion ○ Calc  ○ Calc    ○ Calc  ○ Calc         ○ Calc  ○ Calc
○ Mass  ○ Mass   ○ Mass  ○ Mass         ○ Mass  ○ Mass
○ AD    ○ AD     ○ AD    ○ AD           ○ AD    ○ AD
○ Arch  ○ Arch   ○ Arch  ○ Arch         ○ Arch  ○ Arch ○ Calc  ○ Calc   ○ Calc  ○ Calc         ○ Calc
○ Mass  ○ Mass   ○ Mass  ○ Mass         ○ Mass
○ AD    ○ AD     ○ AD    ○ AD           ○ AD
○ Arch  ○ Arch   ○ Arch  ○ Arch

Right Breast                Left Breast

*Size of Abnormality
○ <1cm  ○ 1-2cm  ○ 2-3cm  ○ <3cm
○ other [ ] cm

*Recommendations:
☐ Ultrasound
☐ Spot compression views
☐ 90° lateral view
☐ Cranio-caudal roll views
☐ Magnification views (cranio-caudel and 90° lateral)

[Add] [Finish] [Cancel]

| Preview Patient Letter |

December 05, 2005
Tracy Johnson
65432 Cavell Circle
Hopkins, HI-54632

Dear Ms. Johnson,

Regarding the following procedure(s)
12/05/2005 BILATERAL SCREENING MAMMOGRAM

Thank you for your recent visit to our facility.

Your digital mammogram shows no evidence of malignancy.

Screening mammography is important to your on going health. Please remember that some cancers cannot be found by mammography, and that early detection requires a combination of monthly self examination, yearly clinical examination, and mammography. For all women over the age of 40, the American Cancer Society recommends a mammogram every year.

I therefore recommend that you have another mammogram in one year.

Your mammogram was provide at Health Care and is being stored with a copy of the report, at 10201 wayzata blvd, Minnetonka, MN 55305. When you obtain your next mammogram, it will be your responsibility to tell the provider when and where you had this mammogram.

Please continue regular breast self-examination and report any changes that concern you, even before your next appointment.

Fig. 27

2800 

| Exam Report Preview | |
|---|---|
| Patient Name | Tracy Johnson |
| MRN | 000197 |
| Patient ID | 110000000000097 |
| Referring Physician | Romeo Drake |
| Additional Physicians(s) | Timothy Montague, M,D. ⌄ |
| DoB: | 08/13/1945 60F |
| Examination Date | 12/30/2005 |

SCREENING MAMOGRAM

Digital images were obtained.
There are scattered fibroglandular densities.

FINDINGS:
There are no suspicious findings.

IMPRESSION:
No Mammographic evidence of malignancy and no significant change.

RECOMMENDATIONS:
A mammogram in one year is recommended

ACR Bi-Rads® Category 1   Negative Exam.

These results and recommendations were sent to the patient.
Thank you for the referral of Tracy Johnson

| Device | | | | |
|---|---|---|---|---|
| Name: | Device ID: | Vendor: | Model: | Facility: |
| Selenia 1 | X343453 | LORAD | Selenia | Goodhealth Clinic - Roseville, MN |

Weekly Signal-to-Noise & Contrast-to-Noise Worksheet

| Field Name | Value | Units | Expected format |
|---|---|---|---|
| Date of Test: | 3-12-2005 | date | mm-dd-yyyy |
| Comments: | | | Text |
| *SNR Mean Beside Disk Reading: | | cm | Decimal |
| SNR Standard Deviation Beside Disk: | | cm | Integer |
| CNR Mean Inside Disk Reading: | | cm | Decimal |
| Disk Warning Indicator On: | ○ Yes  ○ No | | Yes/No |

[ Save ]  [ Cancel ]

SYSTEM AND METHOD FOR TRACKING MEDICAL IMAGING QUALITY

CROSS-REFERENCE TO RELATED APPLICATIONS

This application claims the benefit of U.S. Provisional Application No. 60/742,668, filed Dec. 6, 2005, and U.S. Provisional Application No. 60/613,054, filed Jan. 19, 2005, and the contents of which are incorporated herein in their entirety.

BACKGROUND OF THE INVENTION

Current breast imaging technology presents a variety of challenges for those involved with the practice of mammography. Among those challenges are low reimbursement rates, diminishing availability of fellowship trained radiologists, decreasing numbers of mammography facilities, integration complexity, high cost of human resources and errors, and MQSA compliance. Additionally, despite the growth in full-field digital mammography, the introduction of digital imaging has provided a variety of opportunities to breast imaging technology that have not been fully realized.

BRIEF SUMMARY OF THE INVENTION

In accordance with one embodiment of the present invention, a method in a computer system is provided for managing mammography examination information. The method includes receiving electronically personal information of a patient, such as name, demographic information, and insurance information. Next, digital mammography images of the patient are produced by a modality for a screening examination and/or diagnostic examination, and mammography procedure results data is generated that reflect the results of a procedure examination, such as a biopsy. Then, the personal information, digital images, and procedure data of the user are stored in a database and are logically linked to each other.

When a system user, such as a radiologist, is prepared to interpret examination results, the digital images and procedure data of the user are electronically displayed to the user responsive to a user request. At least a first portion of the digital images is electronically retrieved from the database, and at least a second portion of the digital images is retrieved from a Picture Archive and Communications System (PACS). Data from the user representing a medical interpretation of said digital images and procedure data are received, and a medical report based on the medical interpretation is automatically generated responsive to receipt of the interpretation.

BRIEF DESCRIPTION OF THE DRAWINGS

FIG. 6 is a diagram of an exemplary user interface for a facility schedule configuration screen in accordance with one specific implementation.

FIG. 8 is a diagram of an exemplary user interface for a create appointment dialog screen in accordance with one specific implementation.

FIG. 9 is a diagram of an exemplary user interface for a view appointment dialog screen in accordance with one specific implementation.

FIG. 13 is a diagram of an exemplary user interface for a create exam screen in accordance with one specific implementation.

FIG. 14 is a diagram of an exemplary user interface for a start exam screen in accordance with one specific implementation.

FIG. 16 is a diagram of an exemplary user interface for a search exam screen in accordance with one specific implementation.

FIG. 17 is a diagram of an exemplary user interface for a search exam screen in accordance with one specific implementation.

FIG. 19 is a diagram of an exemplary user interface for a facility dashboard screen in accordance with one specific implementation.

FIG. 20 is a diagram of an exemplary user interface for a study worklist screen in accordance with one specific implementation.

FIG. 21 is a diagram of an exemplary user interface for a compare/repeat exam list screen in accordance with one specific implementation.

FIG. 22 is a diagram of an exemplary user interface for a draft exam list screen in accordance with one specific implementation.

FIG. 23 is a diagram of an exemplary user interface for a callback exam list screen in accordance with one specific implementation.

FIG. 25 is a diagram of an exemplary user interface for an exam results screen in accordance with one specific implementation.

FIG. 26 is a diagram of an exemplary user interface for an add lesion screen in accordance with one specific implementation.

FIG. 27 is a diagram of an exemplary patient letter screen in accordance with one specific implementation.

FIG. 28 is a diagram of an exemplary exam report screen in accordance with one specific implementation.

FIG. 29 is a diagram of an exemplary user interface for a view exam screen in accordance with one specific implementation.

FIG. 31 is a diagram of an exemplary user interface for a diagnostic exam results screen in accordance with one specific implementation.

FIG. 33 is a diagram of an exemplary user interface for a view diagnostic exam screen in accordance with one specific implementation.

FIG. 35 is a diagram of an exemplary user interface for a procedure exam results screen in accordance with one specific implementation.

FIG. 36 is a diagram of an exemplary user interface for a view procedure exam screen in accordance with one specific implementation.

FIG. 40 is a QC Worksheet Screen.

FIG. 41 is a QC Dashboard Screen.

DETAILED DESCRIPTION OF THE INVENTION

System and Method Overview

The mammography management system and method of the present invention is a network-based solution that facilitates secure and efficient electronic data movement. Because the system platform may be implemented in a web-based environment, it promotes access flexibility, wherein users such as radiologists may connect and access the system resources from any connected location. The system provides various functionalities described herein relating to mammography exams and information management and supports full-field digital mammography (FFDM).

The mammography management system and method of the present invention is readily integrated with Picture Archive and Communications Systems (PACS), Hospital Information Systems (HIS), and Radiology Information Systems (RIS), allowing for existing systems to continue to function with the additional benefits of the mammography management system of the present invention. HIS and RIS contain patient and examination information, which are described in more detail below. When resources within the mammography management system and PACS are connected to a HIS/RIS, the mammography workflow is made more efficient by electronically transferring patient and examination data and information to the appropriate workstation/user in the system of the present invention.

PACS is an image management and communication system that stores and distributes digital images and is in communication with the mammography management system. By integrating with PACS, the mammography management system receives electronic image studies from PACS, which in turn triggers the advancement of the exam workflow. Images are generally maintained and transferred using the Digital Imaging and Communications in Medicine (DICOM) standard, where DICOM is a protocol based standard that facilitates the transfer of digital images and associated information between devices.

As described in more detail below, the mammography management system of the present invention electronically associates studies received from the modality with the study request record, the exam, and the patient stored in the system. An integrated PACS system allows for digital image capture and storage, which are then automatically associated with patient exams, or allows for scanning of analog images for comparison with more recent digital images. By electronically associating images and other information received by the mammography management system from PACS or other systems, image retrieval, reporting, and other functionality are enhanced and made more efficient.

Figure 1:
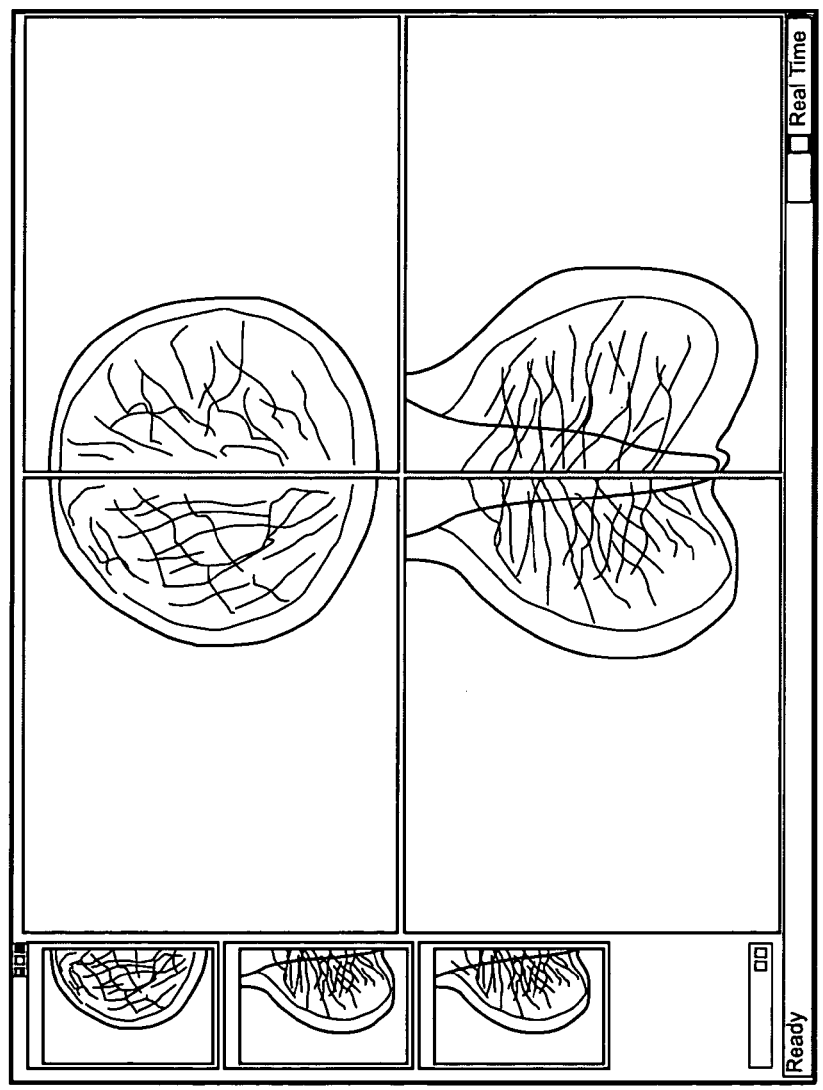
FIG. 1 is a diagram of an exemplary user interface for an image viewing software screen in accordance with one specific implementation.

The mammography management system is also integrated with image viewing software appropriate for viewing mammography studies. A screenshot of an appropriate viewing application is shown in FIG. 1. The software is enhanced to allow for expedient transfer of medical images over the networked connections and resources. This integration also allows for a system user, typically a radiologist, to instantaneously retrieve and view studies, and to automatically load related studies into the viewing software onto suitable viewing station hardware that is appropriately configured. As described in more detail below, image viewing is integrated with the exam workflow such that when a radiologist views exam data, the images are automatically displayed to him or her.

The mammography management system further includes electronic interfaces to various modalities, such as FFDM, sonography, bone density, soft copy workstations (radiologist image viewer), and MRI modalities. As described in more detail below, the present invention includes a variety of worklists that define and prioritize workflows for various activities or actions that will be performed. Where appropriate, the system provides for electronic interfaces with the modalities that allow for modality worklist download, thereby streamlining operations involving the various modalities.

As described in more detail herein, the system of the present invention may also include integration with various other components, including integrated digital signature capture for patients and physicians, integrated voice dictation for physicians, automatic PDF file generation of reports and letters, integrated fax solution for physician reports, and integrated MQSA reporting system. The reports and images are made available to referring physicians via an integrated web portal. Additionally, quality assurance and quality control functionality for FFDM, sonography, and breast MRI modalities allows users to maintain patient images, patient data, and modality data in a single system. The system also incorporates MQSA and BI-RADS standards, thereby promoting portability and minimizing training time for new users.

System Architecture and User Portals

Figure 2:
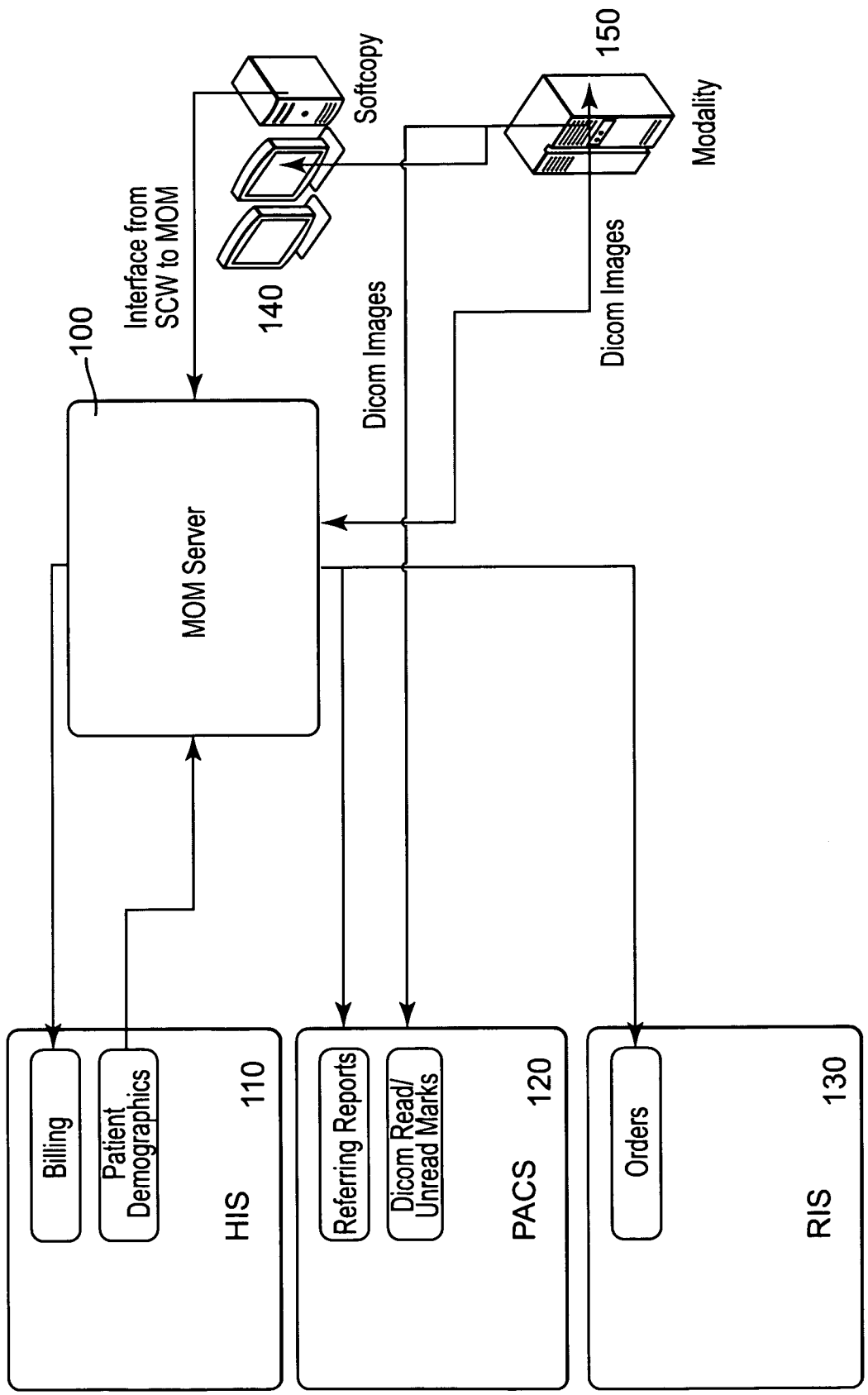
FIG. 2 is a block diagram of an exemplary computer system that can be used to implement various described embodiments.

FIG. 2 shows a logical representation of the architecture of the mammography management system of the present invention in one possible configuration for a hospital implementation. Because the representation is logical rather than physical, those skilled in the art will appreciate that the physical implementation of the mammography management may take the form of a variety of different embodiments, including one or more servers associated with one or more databases and other physical components for performing data management, user interfaces generation, information storage, or performing other operations as described herein. In the configuration shown in FIG. 2, the mammography management system server 100 is integrated with existing HIS 110, PACS 120, and RIS 130 components. The server 100 may be physically located at the hospital facility, remotely located as part of a larger campus, or hosted by a third party. When the server 100 is not local to the hospital or other medical facility, the server and other components of the mammography management system may communicate through a variety of suitable means, such as the Internet, frame relay, point to point networking, or other appropriate architectures. The specific configuration of any installation of the mammography management system may vary while still remaining within the scope of the present invention.

Figure 3:
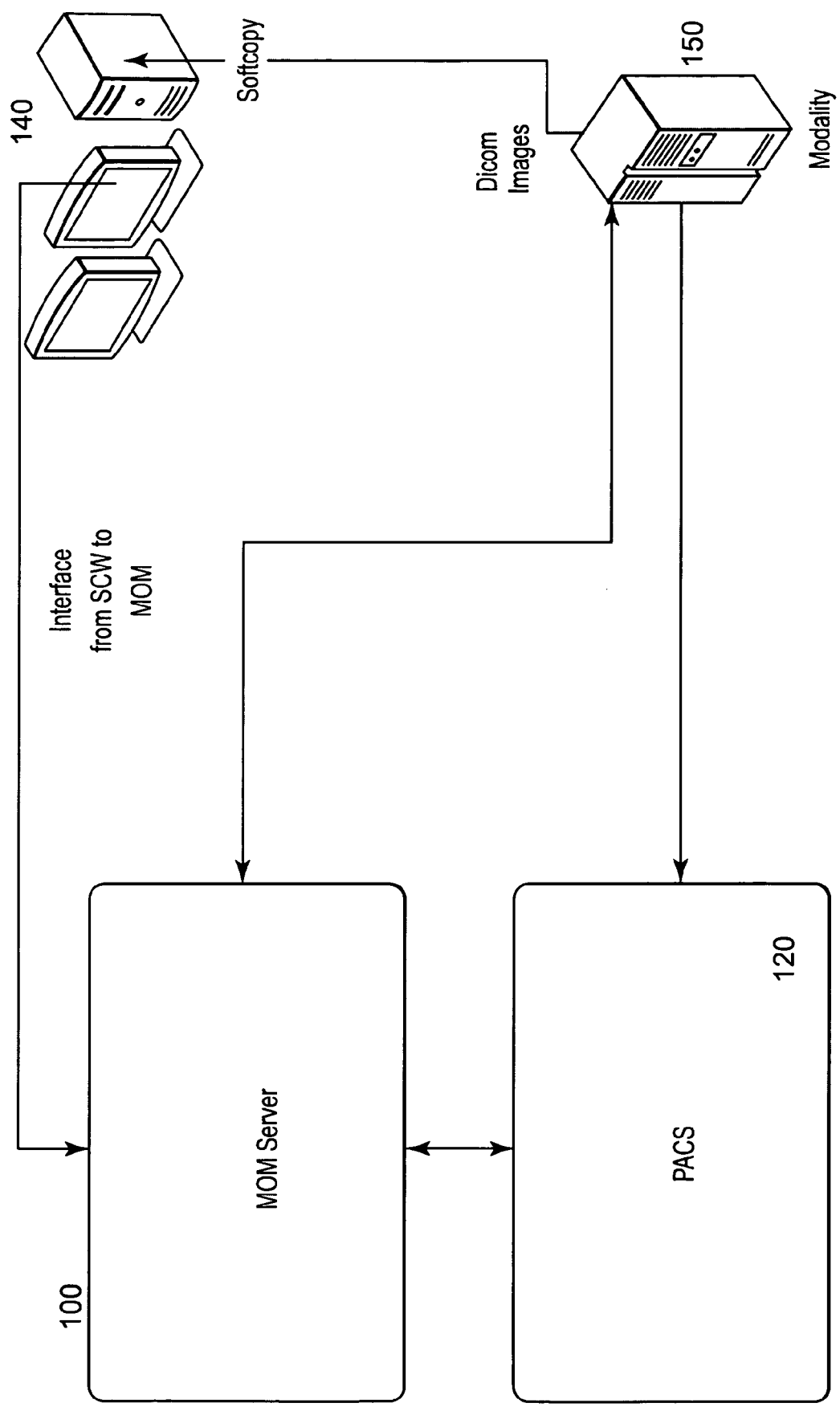
FIG. 3 is a block diagram of another exemplary computer system that can be used to implement various described embodiments.

FIG. 3 shows a logical representation of the mammography management system in one possible configuration for a free-standing facility implementation. In the configuration shown in FIG. 3, the mammography management system server 100 is integrated with an existing PACS component 120. In this embodiment, a user may view DICOM images at soft copy workstation (SCW) 140, provided from server 100 or modality 150. Generally, all code, operating systems, databases, and web servers reside on hard drives local to the server 100.

Figure 4:
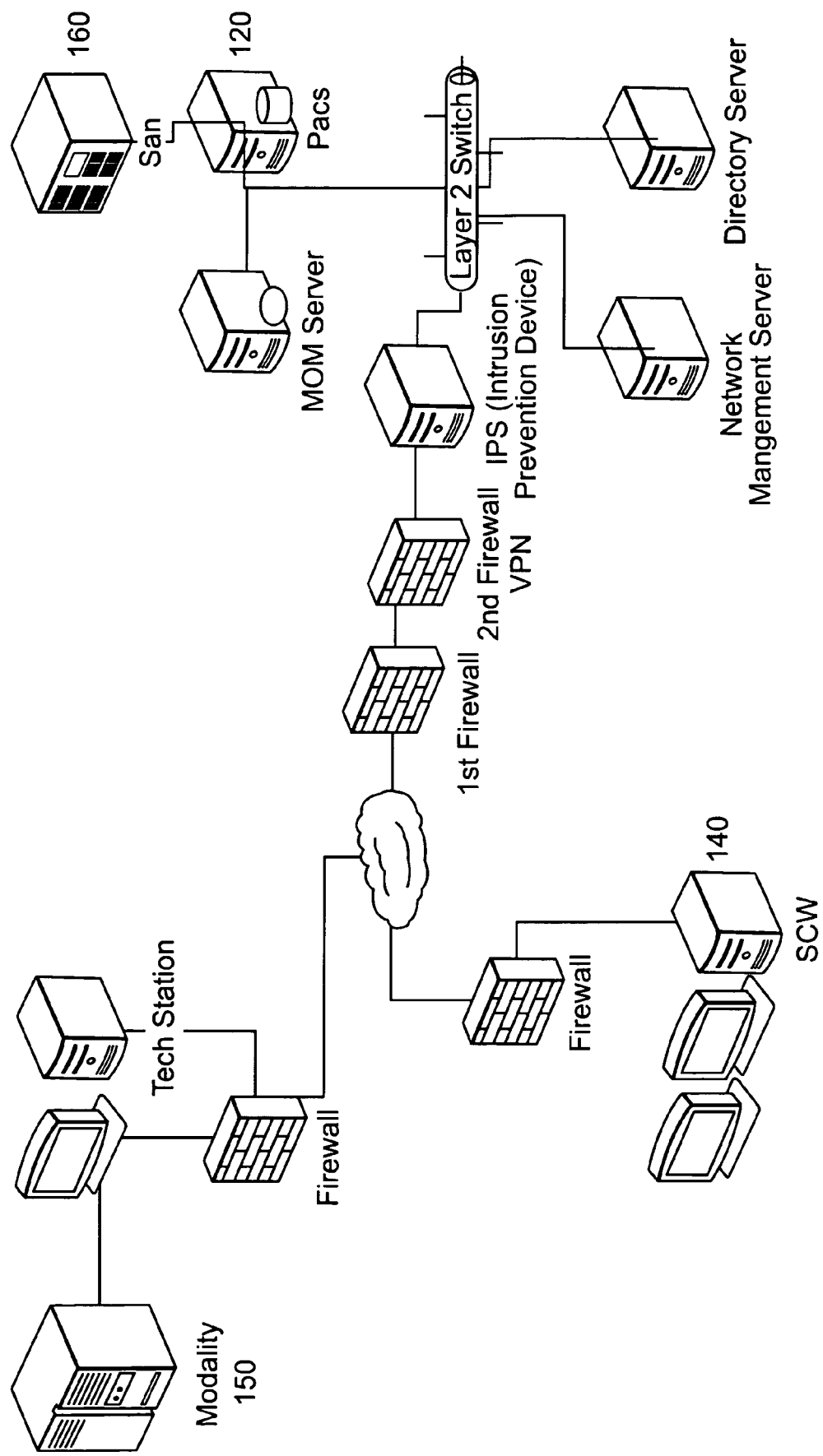
FIG. 4 is a block diagram of yet another exemplary computer system that can be used to implement various described embodiments.

FIG. 4 shows a logical representation of the architecture of the mammography management system in one possible configuration for a satellite mammography screening service implementation. This configuration includes optional on-site and/or off-site storage services, storage area network (SAN) 160, which stores all relevant patient information, such as images, patient data, and exam data. This configuration allows a satellite mammography screening facility and service to benefit from the desired functionalities of a third party provider of the mammography management system.

Users of the system may include a variety of individuals such as radiologists, technologists, administrators, referring physicians, clerical and other facility employees, and, in some instances, patients (e.g., to sign or view disclosure information). As illustrated above, various system architectures are envisioned within the scope of the present invention, and the various system users may access the system from a variety of resources and locations. For example, a technologist may interact with the system via system interfaces provided at any number of tech stations located within a facility, whereas a radiologist may interact with the system via system interfaces provided at either a soft copy workstation at a facility or at an Internet-connected computer at the radiologist's home. The architecture flexibility allows for accommodating any desirable configuration of such portals or access points to the mammography management system.

Users of the mammography management system connect to the system by first logging in to a system portal or access point prior to using any of the management system functionality. The login requires authentication of the user and provisioning of user privileges based on his or her assigned role. In order to access the portal the user must provide his or her username, password, and an optional crypto key. Successful login will establish a trusted session with the system portal.

Access and login may be performed through a user interface via a web browser. When the username, password and crypto key number are authenticated by the mammography management system server 100, the appropriate screen is displayed based on the user's predefined role. Predefined roles and corresponding screens may include the following: administrator/patient search screen; radiologist/pending exam screen; lead interpreting physician/exam search screen; system administrator/user search screen; and referring physician/exam search screen. For example, when an authorized radiologist logins, a "pending exam" screen will be displayed.

Figure 5:
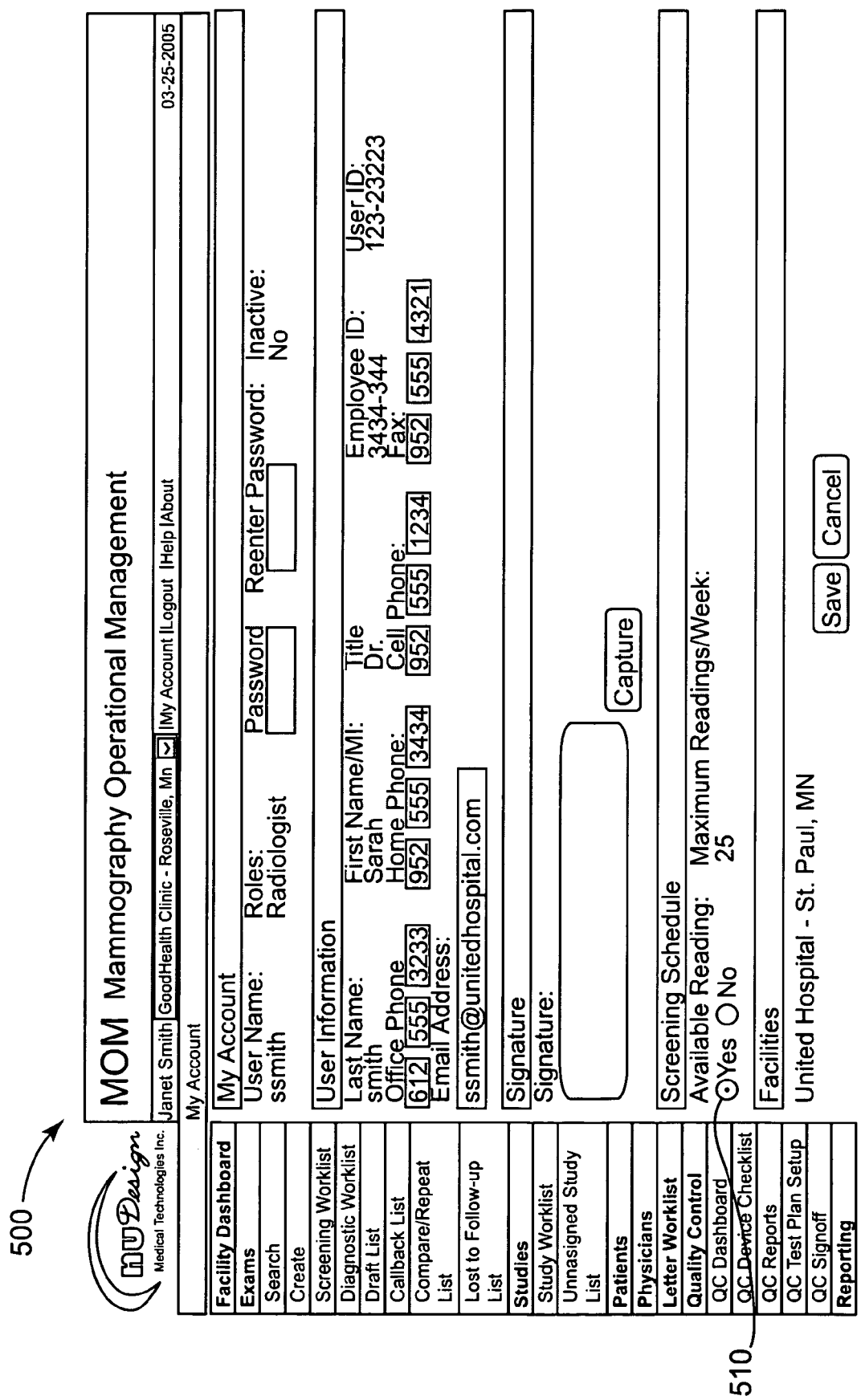
FIG. 5 is a diagram of an exemplary user interface for a user account screen in accordance with one specific implementation.

With reference to FIG. 5, a user account screen 500 allows a user to manage various information including office phone, home phone, cell phone, fax, email address, and password. Additional display of signature, screening schedule, facilities and linked physician record are dependent on the account options for the user's roles. For example, for users identified as radiologists, a selection is made available for toggling a "Available for Reading" setting 510, which indicates whether the radiologist is available to review studies.

System Exam Scheduling Functionality

The mammography management system appointment scheduling component provides a facility with appointment scheduling functionality. The system provides each facility with a separate schedule of appointments across the facility's defined resources. A resource is a generic term for an entity that may be scheduled, such as staff, rooms, and equipment.

The scheduling functionality provides interfaces for a user to schedule patient appointments to a specific resource/time intersection. An appointment represents the time and resource at which a study will occur for a patient. The scheduling component of the mammography management system also maintains a schedule for each facility and allows a user to limit the user or availability of resources to certain types of studies. The functionality further provides user interfaces that display lists of first available appointments and that allow a user to select existing patients stored in the mammography management system or create new patients when an appointment is scheduled. The scheduling functionality integrates appointments with the exam/study creation processes described below to exchange data and automatically populate fields containing previously acquired data.

Figure 6:
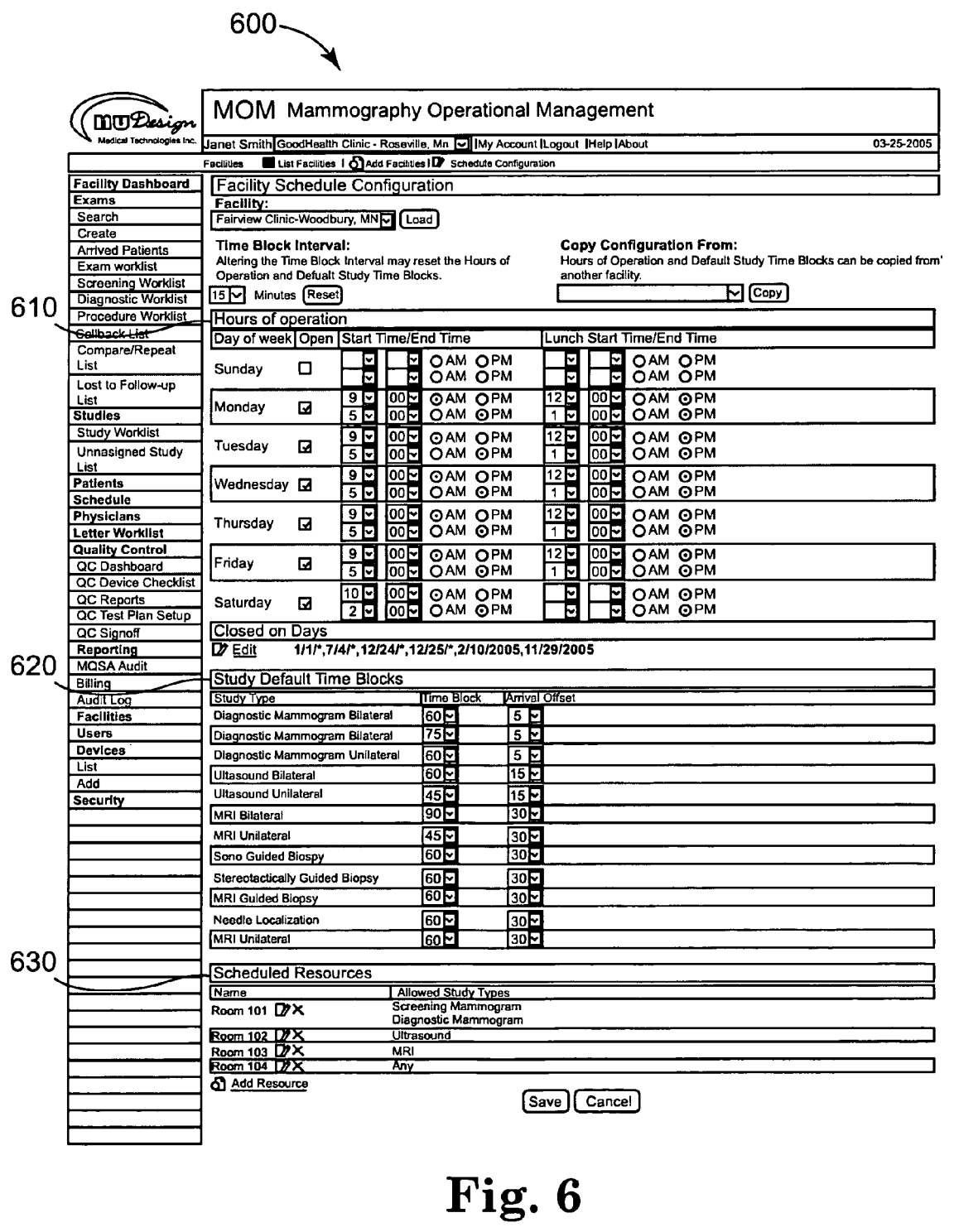
Figure 7:
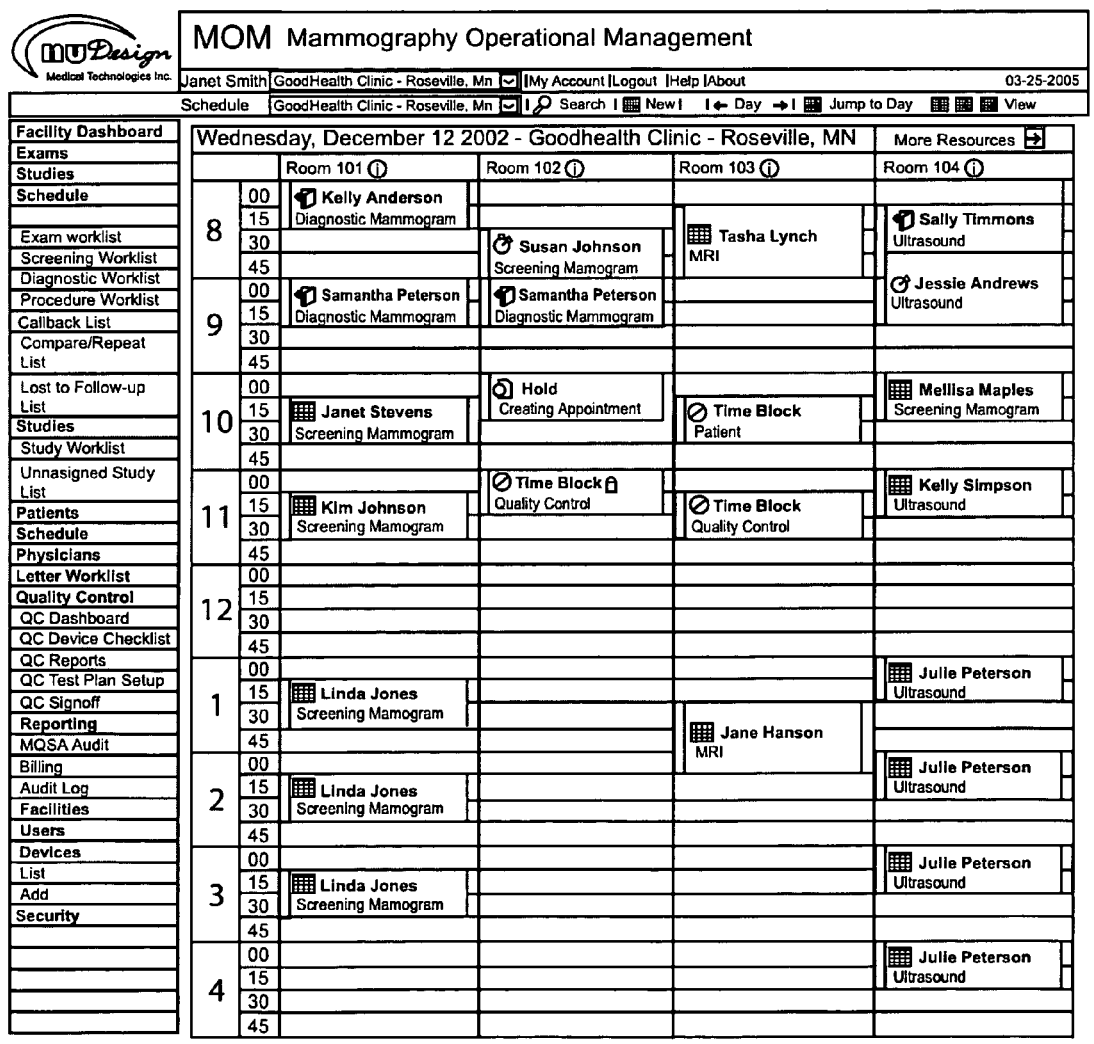
FIG. 7 is a diagram of an exemplary user interface for a schedule day view screen in accordance with one specific implementation.

The mammography management system appointment scheduling user interface provides for various views/screens relating to scheduling to accomplish the forgoing functionality. The Schedule Configuration screens allow the system user to configure hours of operation 610, time segmentation 620, and scheduled resources 630. An example of a Facility Schedule Configuration screen 600 is seen in FIG. 6. These configurations are performed at the facility level. The Schedule View screens display to a user the appointment schedule for a specific facility through different views based on time span (e.g., daily, weekly, bi-weekly). An example of a Schedule Day View screen 700 is seen in FIG. 7. The schedule view screens may also be used to locate and schedule new appointments. The Appointment screens display an interface for creating, modifying, viewing and searching for patient appointments. An example of an incomplete Create Appointment Dialog screen 800 is seen in FIG. 8, and an example of a View Appointment Dialog screen 900 is seen in FIG. 9. The Appointment screens allow a user to link an appointment to an existing patient record stored in the mammography management system.

Figure 10:
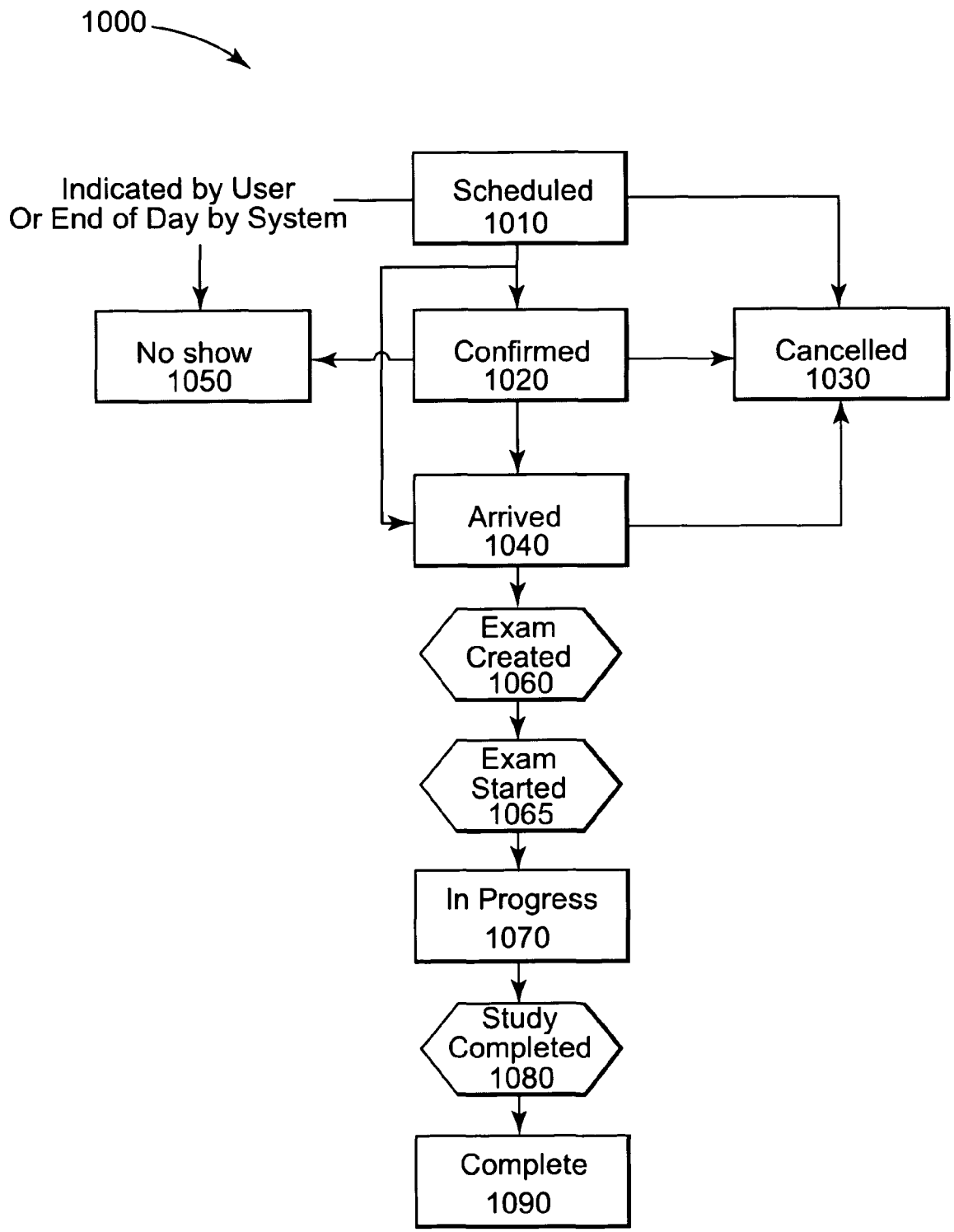
FIG. 10 is a flow diagram that describes steps in a appointment workflow method in accordance with one described embodiment.

With reference to FIG. 10, the Appointment Workflow 1000 in accordance with one embodiment of the present invention is shown, illustrating the appointment statuses throughout the workflow. Typically, a patient calls a facility's appointment desk, and a "scheduler" or other system user answers the phone, determines basic information about the appointment (e.g., type of study, which breast) and uses the Schedule View screens to locate an appropriate time slot. The scheduler then locates the existing patient in the mammography management system, creates a new patient, or takes basic information, enters the referring physician, saves the appointment using the Appointment Screens. At this point, the appointment is given a status in the mammography management system of Scheduled 1010. If the patient information was not previously stored or located in the mammography management system, the scheduler or administrator user adds the new patient to the system by navigating to the patient area and clicking on the "add" link in the patient search screen.

Optionally, a facility employee can call the patient to confirm the appointment prior to the actual appointment date/time. At this point, the appointment is given a status in the mammography management system of Confirmed 1020. Prior to the appointment the patient may also call and cancel the appointment. The scheduler or other user of the system enters the cancellation into the mammography management system, and the appointment is given a status in the system of Cancelled 1030.

If the patient keeps the appointment, the patient typically arrives at the facility and checks in with a front desk employee who enters the arrival into the mammography management system. At this point the appointment is given a status in the system of Arrived 1040, and a related exam is created in the mammography management system as described in more detail below. The mammography management system user may also update the patient record with additional demographic or insurance information. If the patient does not show up at the scheduled time, the system user may mark the appointment as a "No Show" with a like status 1050.

When the appointment is in Arrived status, the mammography management system employ the patient and appointment information to pre-create an exam 1060, as described in more detail below. A Create Exam screen is displayed to the user for verification and/or modification of the data fields. During this process an association between the Exam and the Appointment is created in the mammography management system database.

When the exam related to the appointment is started 1065 by a technologist and is so indicated in the system, the appointment is automatically given a status in the system of In Progress 1070. When the study related to the appointment is completed 1080 by the Technologist and is so indicated in the system, the appointment is automatically given a status of Completed 1090.

System Exam Functionality

Figure 11:
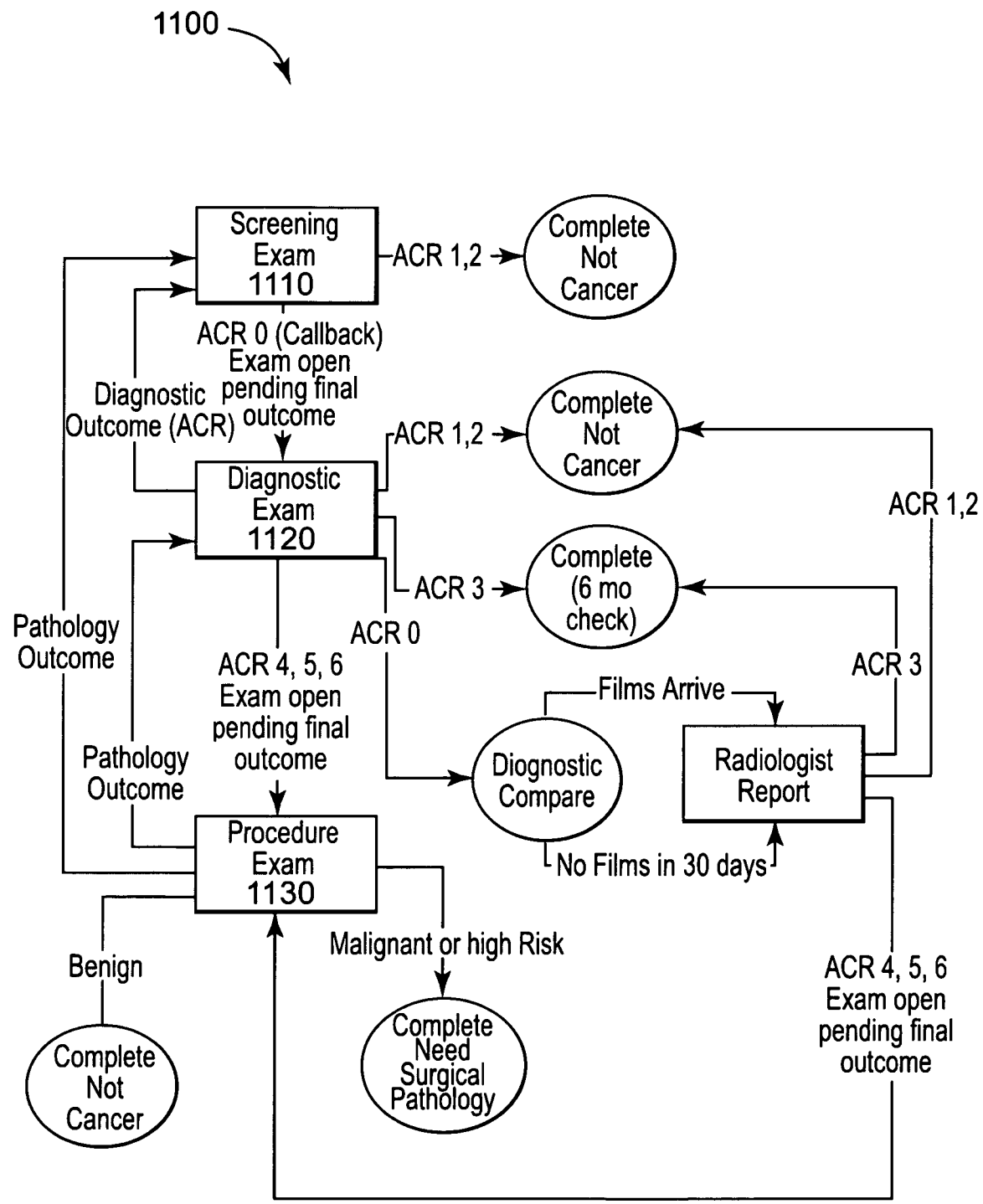
FIG. 11 is a flow diagram that describes steps in a method for performing screening, diagnostic, and procedure examinations in accordance with one described embodiment.

The mammography management system provides support and management functionality for mammography screening exams, diagnostic exams, and procedure exams. FIG. 11 depicts a procedural flow chart 1100 of screening, diagnostic and procedure exams and ACR results in an overall flow through one embodiment of the mammography management system. First, a screening exam 1110 may be scheduled and managed in the mammography management system. When the screening exam uncovers an abnormality (e.g., ACR 0), the exam is recorded as a callback result. The patient is then scheduled to obtain a diagnostic exam 1120. The diagnostic exam may also be scheduled and managed in the mammography management system. Depending on the results of the diagnostic exam (e.g., ACR 4, 5, 6), the patient may subsequently require a procedural exam 1130, such as a biopsy. The procedural exam 1130 may also be managed in the mammography management system. Managing all such exams in the mammography management system allows the system to link each of the patients and exams together and feed back the final outcome data to the relevant individuals as described in more detail below.

Figure 12:
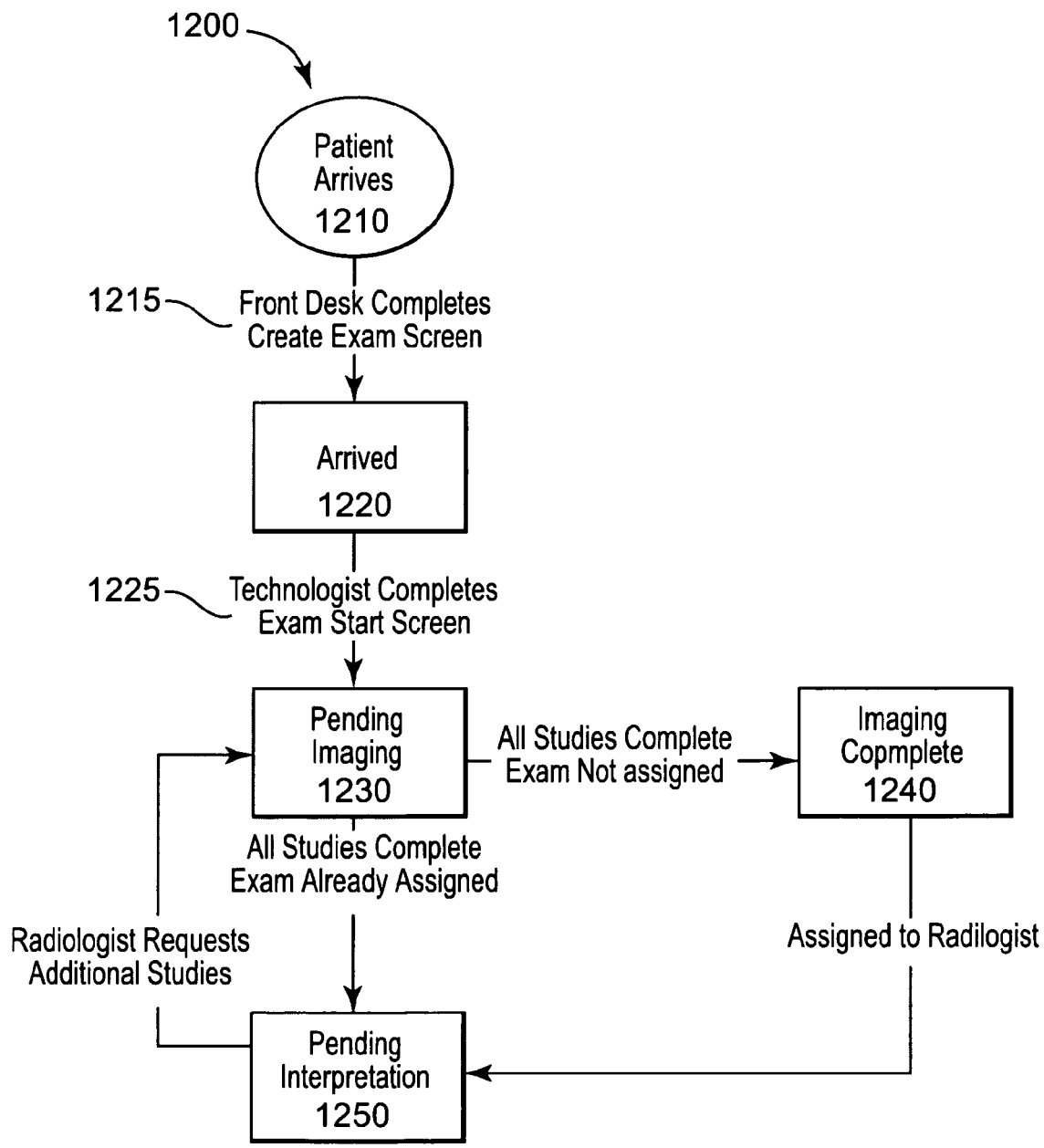
FIG. 12 is a flow diagram that describes steps in a method for creating an exam record in accordance with one described embodiment.
Figure 13:
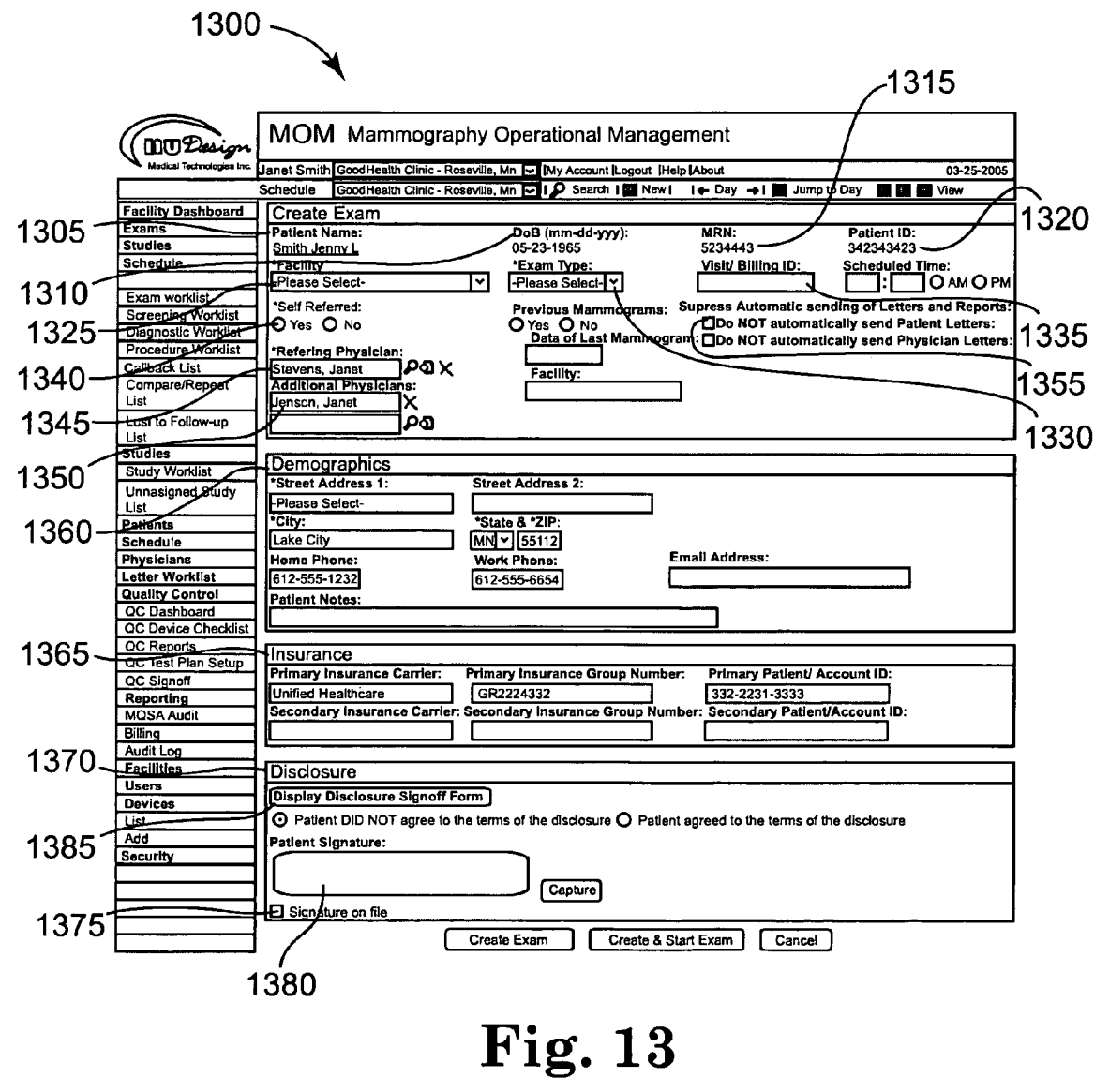

With reference to FIG. 12, a procedural flow chart 1200 is shown for the exam creation process for each of the three exam types described above. After a patient physically arrives 1210 at the exam location, a front-desk user of the mammography management system creates the basic exam 1215 information by completing a "create exam" screen of the mammography management system, which includes verifying patient demographic and insurance data and obtaining disclosure sign off from the patient. An example of the "create exam screen" 1300 is shown in FIG. 13 and is described in more detail below. After completion of the "create exam screen", the patient's visit is recognized by the mammography system is in the "arrived" state 1220. The "arrived" designation indicates in the mammography management system that the patient is physically present for the exam to be created, but no studies have yet been requested. In one embodiment of the present invention, the patient is in a waiting room when her exam is in the "arrived" state.

Seen in FIG. 13 is an example of the "create exam" screen 1300 displayed by the mammography management system to a front-desk or other user. The screen 1300 requests the collection of information including, which is then entered into the corresponding fields: patient name 1305, date of birth 1310, 1315, patient ID 1320, facility where exam is being performed 1325, exam type 1330 (screening, diagnostic or procedure), visit/billing ID 1335, scheduled time (time for which the exam is scheduled; may be auto-populated is using the mammography management system scheduler), self referred 1340, referring physician 1345 (may be auto-populated to the patient's primary physician), additional physicians 1350, and suppress automatic sending of letters/reports 1355 checkboxes. The demographics 1360 and insurance 1365 sections of the "create exam" screen 1300 are pre-populated from the selected patient's record. The demographics and insurance data is displayed in order to offer easy confirmation and modification of patient information as needed. The disclosure section 1370 of the "create exam" screen 1300 allows for the mammography management system to track the sign-off of a facility's legal disclosure document. The system allows for (1) the legal disclosure document to be presented on paper to the patient and then gathers the signature on paper, which is indicated by checking the "Signature on File" checkbox 1375, (2) the legal disclosure document is presented on paper to the patient and then obtains the patient's signature electronically from the signature control 1380 on the page, and (3) the legal disclosure is presented electronically to the patient by pressing the "Display Disclosure Signoff Form" button 1385, in which case the electronic disclosure is then displayed to the patient in a popup window with a signature control.

After the exam information is collected the front-desk or other user may either create the exam and cause the patient's status to change to "Arrived" 1220 by pressing the "Create Exam" button or create the exam and then go to the "start exam" page directly by pressing the "Create & Start Exam" button. When either button is pushed the following actions occur: an exam record is transmitted to and created in a mammography management system database, the patient's exam status is set to "Arrived" 1220, an exam audit log entry is made to indicate the creation of the exam, the exam is displayed in the facility dashboard arrived patients section, the exam is displayed on the arrived patients screen for the facility. When the "Create & Start Exam" button is pressed, the "start exam" screen will also be displayed. The "Arrived"

status 1220 is used to represent the exam state after the completion of the "create exam" screen. Each of the exam workflows in the mammography management system (e.g., screening, diagnostic, and procedure), which are described in more detail below, initially start in the "Arrived" status.

Again with reference to FIG. 12, at step 1225 a user of the mammography management system next typically completes the next screen, the "start exam" screen. The "start exam" screen is typically populated by a user such as a technologist who interviews the patient to determine symptoms, patient medical history and required studies. This type of information is traditionally not obtained in the waiting room, but rather a private exam room. Accordingly, the technologist will also have access to a computer connected to the mammography management system with his or her login information. The technologist also requests the initial set of studies to be performed. When the technologist completes the start exam screen, the exam will continue the established workflow paths in the mammography management system.

Figure 14:
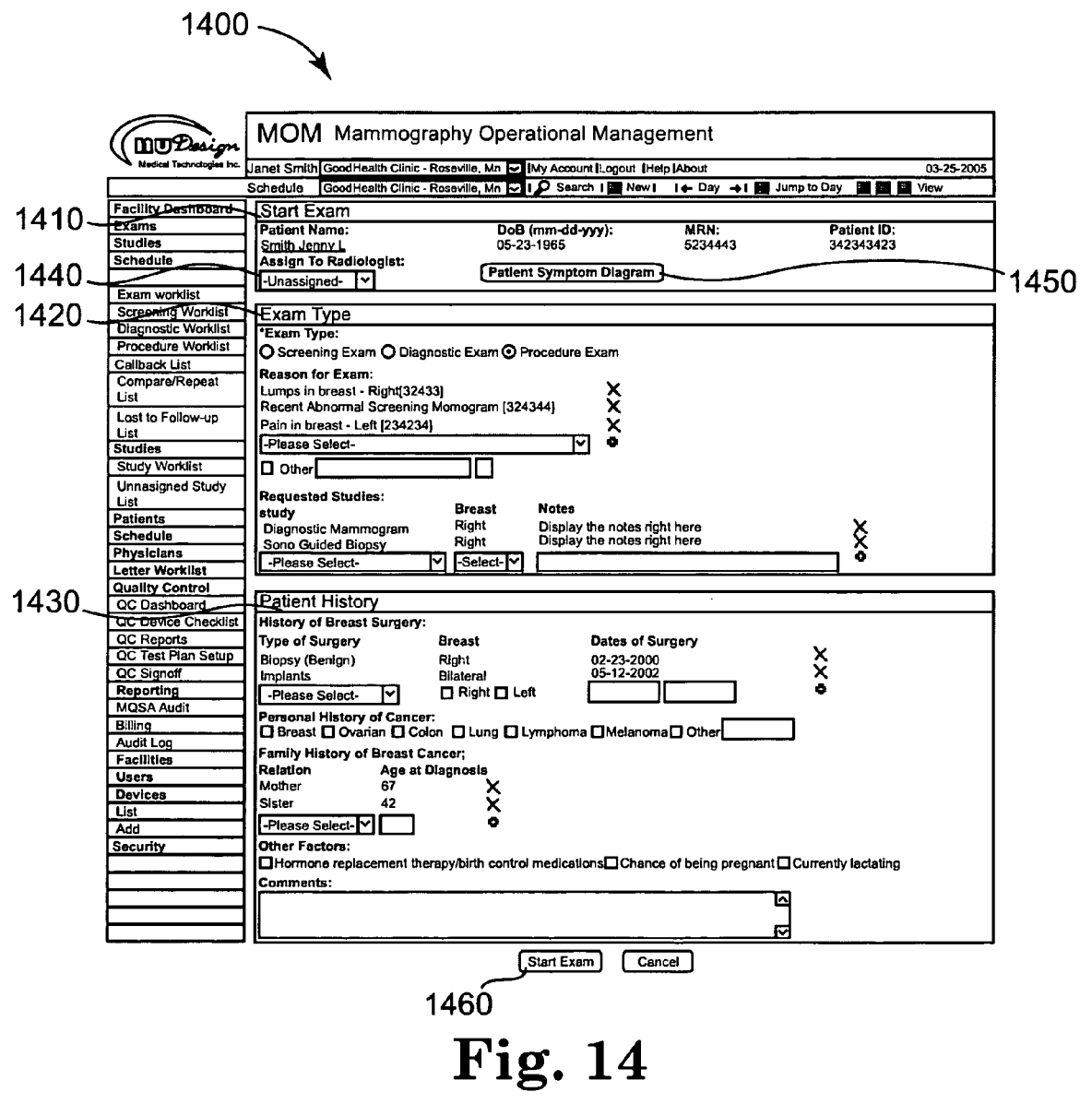
Figure 15:
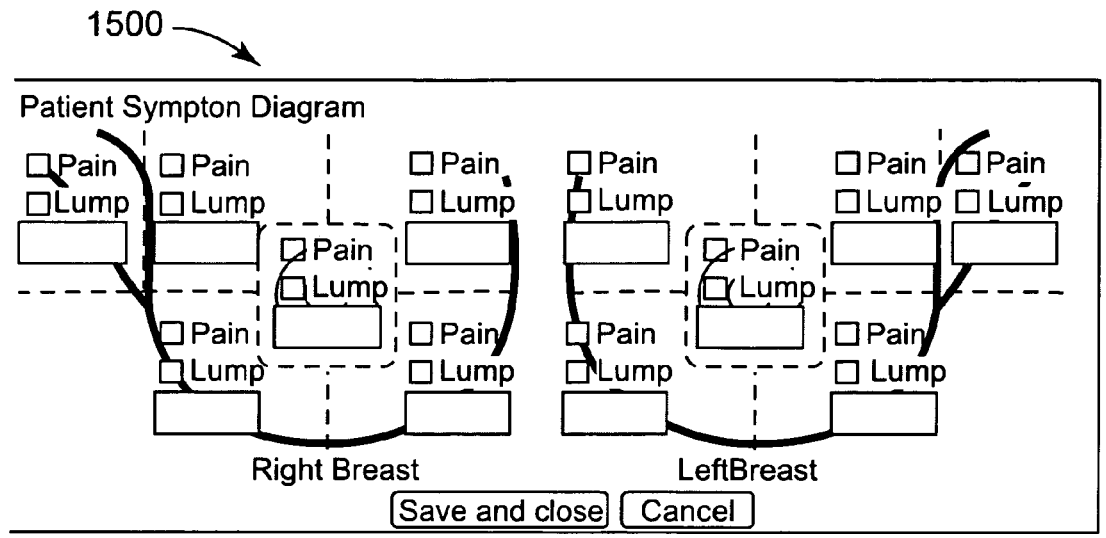
FIG. 15 is a diagram of an exemplary user interface for a symptom recordation screen in accordance with one specific implementation.

FIG. 14 shows a screen shot 1400 of an example "start exam" screen in accordance with the present invention. In this embodiment, the user interface includes three general areas of the screen: "start exam header" 1410, "exam type" 1420, and "patient history" 1430. The "start exam header" section 1410 includes fields for patient name—a field that is dynamically linked to the "view patient" screen—patient date of birth, patient MRN, and patient ID number. The "start exam header" section also includes a field labeled "assign to radiologist" 1440. The "assign to radiologist" listbox 1440 includes a selectable list of radiologist system users who have an association in the system with the facility where the exam is being created and have Exam Results security permission. Selecting a user from the "assign to radiologist" listbox 1440 assigns the current exam to the radiologist-user for the entry of exam results. The "start exam header" section 1410 further includes a "patient symptom diagram" button 1450, the selection of which activates a popup window 1500 that allows for symptom recordation as seen in FIG. 15.

The "exam type" section 1420 of the "start exam" screen 1400 functions substantially similarly as for a diagnostic exam and a procedure exam as described below. The "patient history" section 1430 of the "start exam" screen 1400 functions substantially similarly as for the "create exam" process as described below. The fields in the "patient history" section 1430 are pre-populated with the most recent exam for the patient.

Once the patient data has been entered, the technologist-user may start the exam by pressing the "start exam" button 1460 on the "start exam" screen 1400. Upon selection of the "start exam" button 1460, following actions occur: (1) the entered exam information, including patient history, is transmitted to and updated in a mammography management system database, (2) the exam status is set to "pending imaging" 1230 (seen in FIG. 12), but if studies have been requested by the user or automatically by the system, (3) an exam audit log entry is made to indicate the start of the exam, the studies entered by the user are created in "requested" status, and the exam is removed from the "arrived patients" screen, and the new requested studies are displayed in the "study worklist," and (4) the user interface returns the system user to the Arrived Patients screen. If no studies are requested the exam will remain in the Arrived status 1220. If the user presses the Start Exam button with no studies requested the user receives a confirmation prompt indicating that no studies have been requested for the exam. After the "start exam" screen is successfully completed, the exam is set to "pending imaging" status al230 and continues on the procedural workflow path 1200.

After all relevant patient information is available for the radiologist, but the radiologist has not yet reviewed the information or made a recommendation, the exam status is set to "pending interpretation" 1250. Upon reaching a final conclusion for a study or exam, the radiologist sets the status to "complete."

Figures 16, 17:
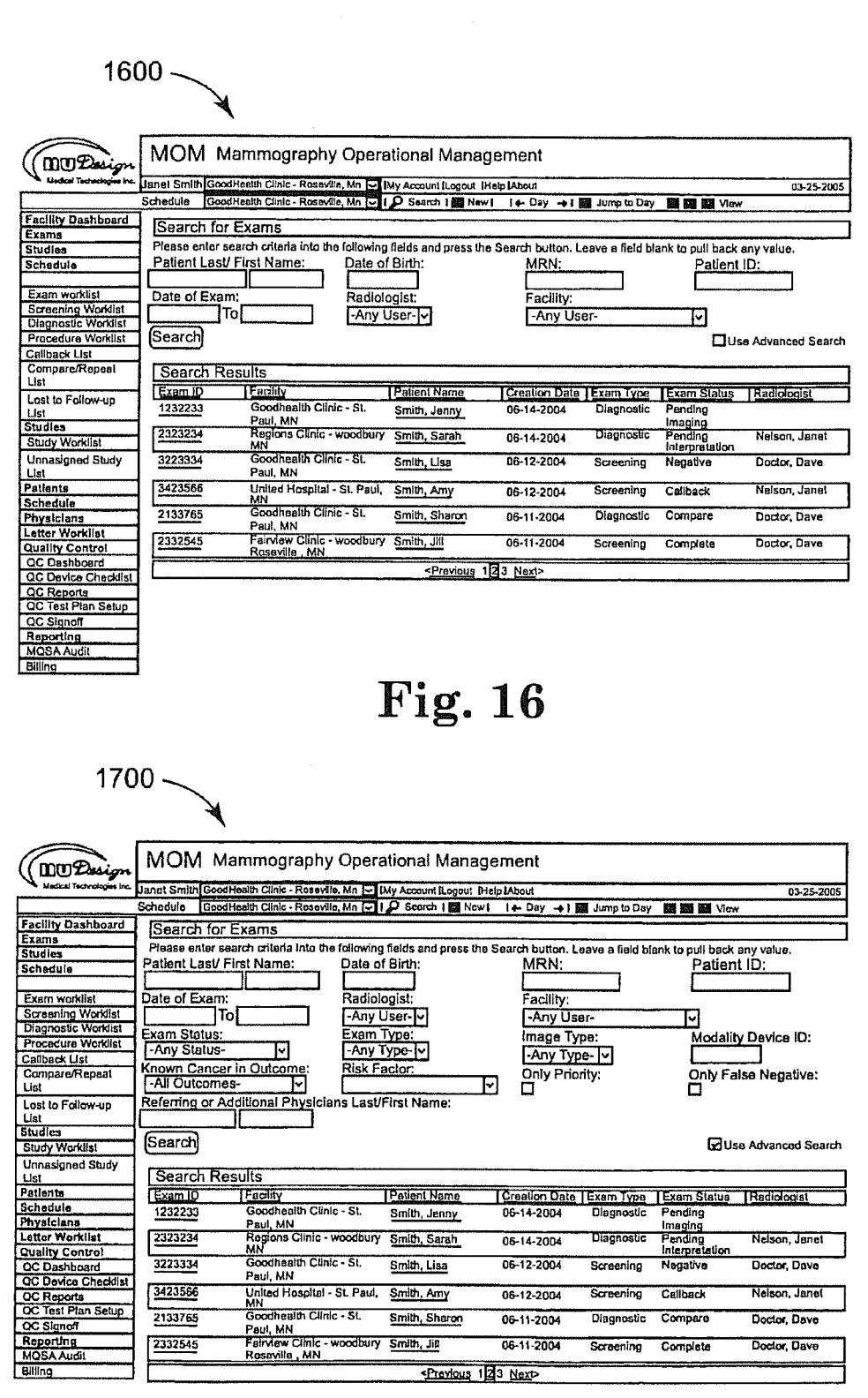

With reference to FIG. 16, which shows one embodiment of the "search exam" screen 1600, and FIG. 17, which shows one embodiment of the "search exam" screen with advance search 1700, the exam search screens allow system users to search for an exam based on entered criteria and displays the matching entries in a paginated result list. The user interface allows system users to search for exams based on the following fields including patient last name and first name, patient date of birth, MRN, patient ID, date of Exam (within a range), radiologist, and facility where the exam is/was performed. The advance search criteria further allow for a system user to search based on the following fields: exam status, exam type, image type, modality device ID, device ID, cancer type, risk factors, referring or additional physician name, priority exams, and exams termed as "false negative." Results of the search are may be sorted based on individual columns of the result listings and appropriate pagination will be provided. This functionality enables additional research capabilities by providing system users to identify patients and patient exam information based on desired criteria. Academic and research facilities may also benefit from this research-supporting functionality.

Worklists

Various worklists are utilized by the mammography management system as described in more detail below. The worklists assist the system users, such as radiologists, and other users involved with the exams, manage patients and exams.

Figure 18:
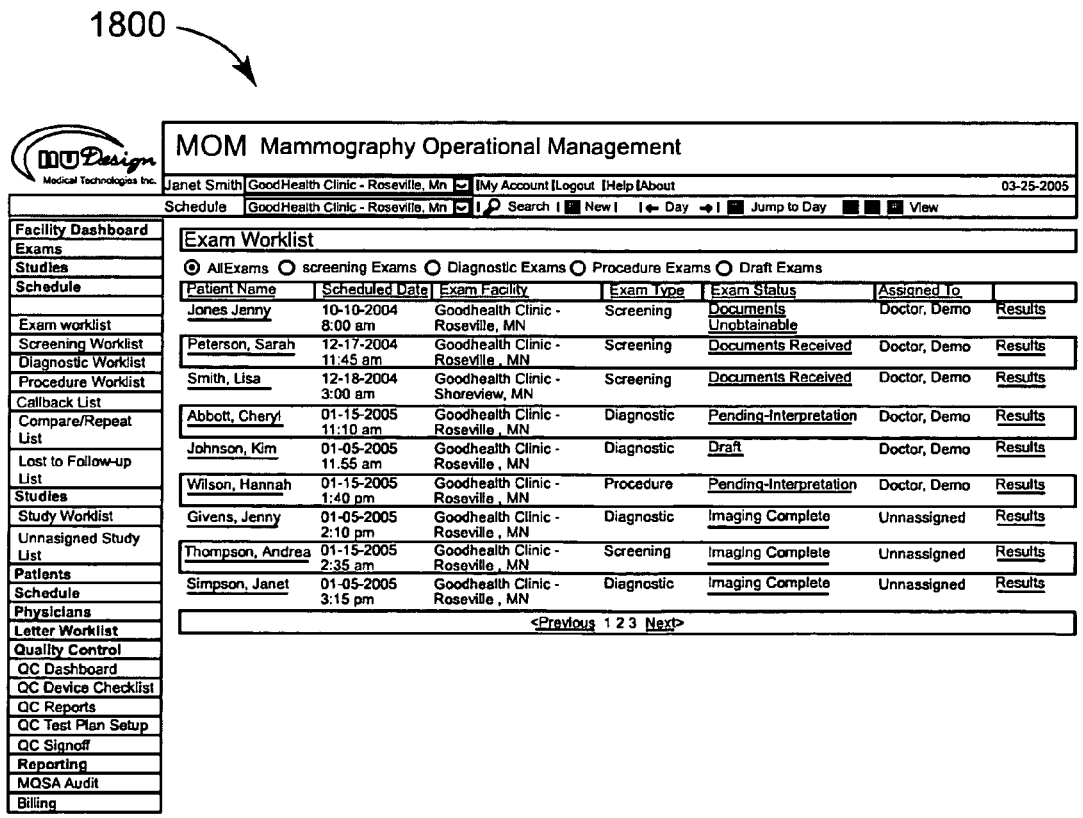
FIG. 18 is a diagram of an exemplary user interface for an exam worklist screen in accordance with one specific implementation.

With reference to FIG. 18, an exam worklist screen 1800 in accordance with one embodiment of the present invention is shown. The exam worklist screen is used to display all exams assigned to a user, typically a radiologist, or exams that are unassigned but occurring at the user's current facility.

Figures 19, 20:
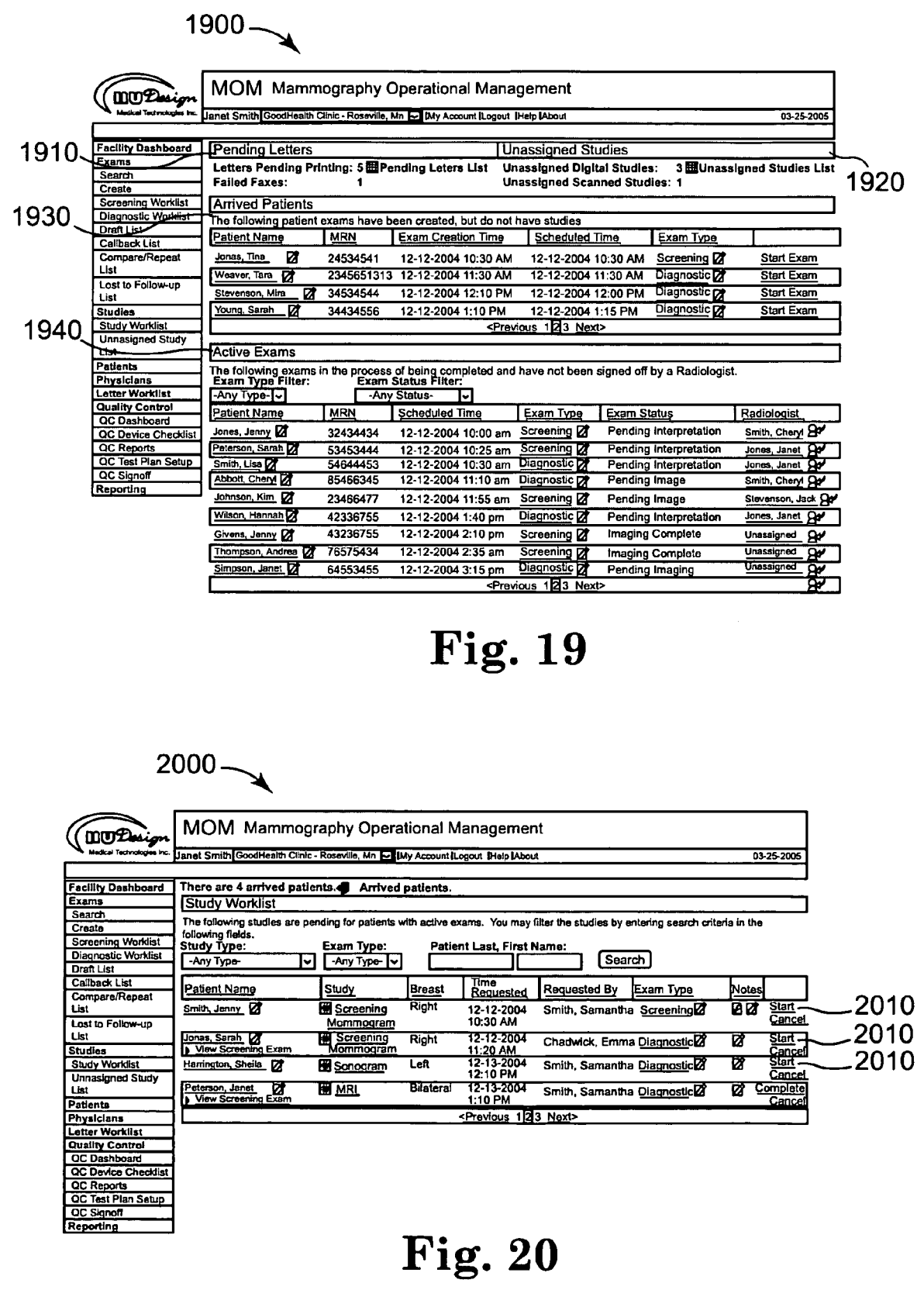

With reference to FIG. 19, a facility dashboard 1900 in accordance with one embodiment of the present invention is shown. The facility dashboard 1900 is a display screen that provides a snapshot of a facility's overall status for the day. Included in the facility dashboard 1900 are a pending letters section 1910 (summary of the patient letters waiting to be printed), an unassigned studies section 1920 (summary of the studies in PACS that could not be automatically associated with an active patient exam in the mammography management system), an arrived patients section 1930 (list of all exams that do not yet have any active or complete studies), and an active exams section 1940 (list of the exams that are currently in progress, i.e., pending interpretation, pending imaging, or imaging complete). The dashboard screen 1900 automatically refreshes at a regular, predefined internal.

With reference to FIG. 20, a study worklist screen 2000 in accordance with one embodiment of the present invention is shown. The study worklist screen 2000 presents a count of arrived patients with links to patients' exam screens. In the procedure exam workflow described below, the technologist can signal the assigned radiologist that a patient is ready for a procedure to begin by selecting the "ready" link 2010 in the study worklist screen 2000 that appears for studies related to procedure exams that are in the "patient prep" status. Responsive to selection of the "ready" link 2010, the status of the related exam is changed to "patient ready," and the study worklist screen refreshes and the "ready" link is no longer be available for the study. The "ready" link 2010 is only relevant to procedure exams and not to diagnostic or screening exams.

Figures 21, 22:
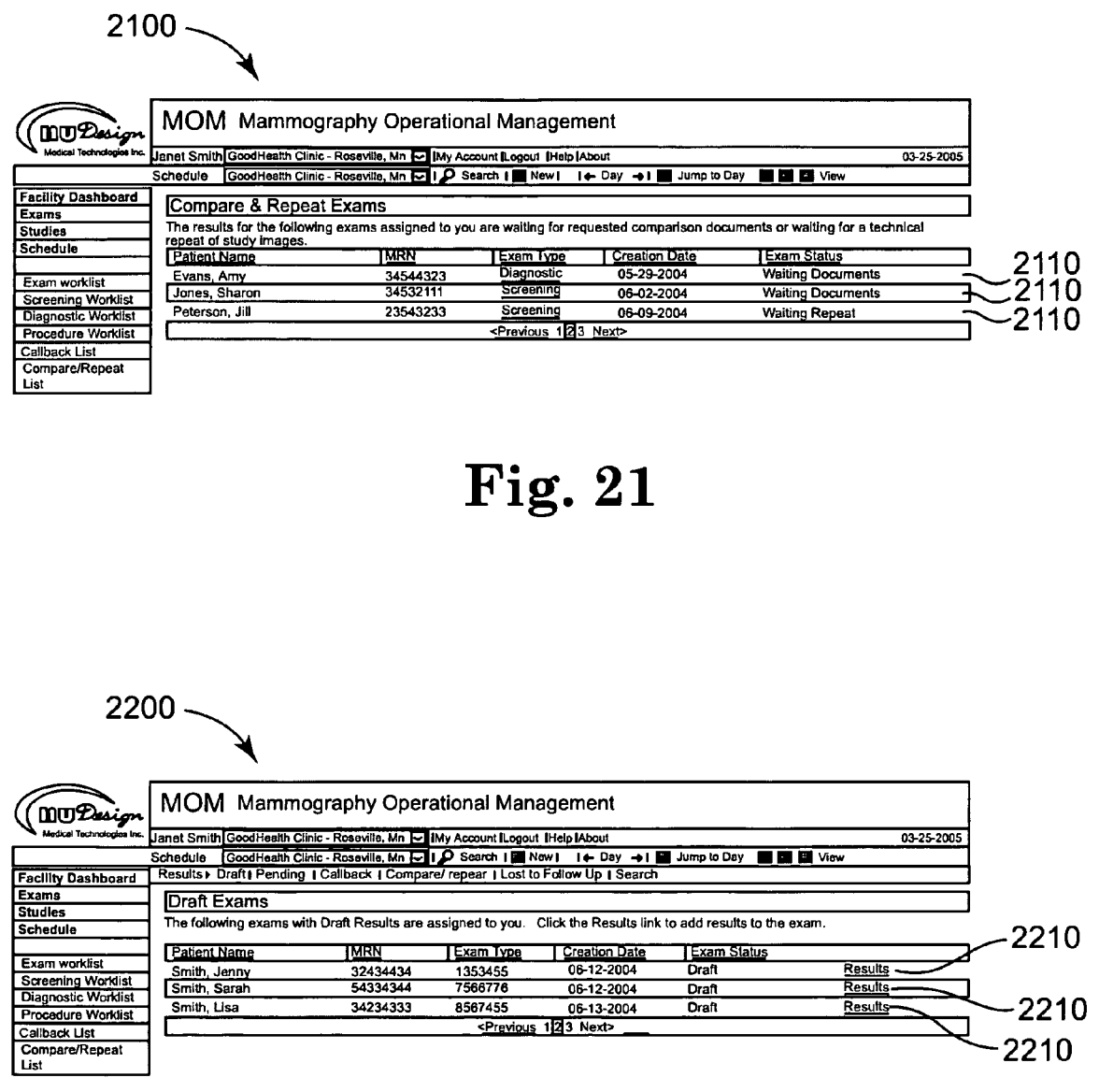

With reference to FIG. 21, a compare/repeat exam list 2100 in accordance with one embodiment of the present invention is shown. The compare/repeat exam list displays all active exams 2110 that the radiologist has previously classified as either "compare" or "technical repeat."

With reference to FIG. 22, a draft exam list 2200 in accordance with one embodiment of the present invention is shown. The draft exam list 2200 displays the exams saved as draft by the radiologist. The radiologist may enter the final results by clicking a "results" link 2210.

With reference to FIG. 23, a callback exam list 2300 in accordance with one embodiment of the present invention is shown. The callback exam list 2300 displays all active exams that the radiologist previously classified as "callback." When diagnostic and pathology reports arrive for these exams the administrator can use the callback exam list to readily locate the exam and open the final outcome screen by selecting the corresponding "final outcome" link 2310.

Screening Exams

Figure 24:
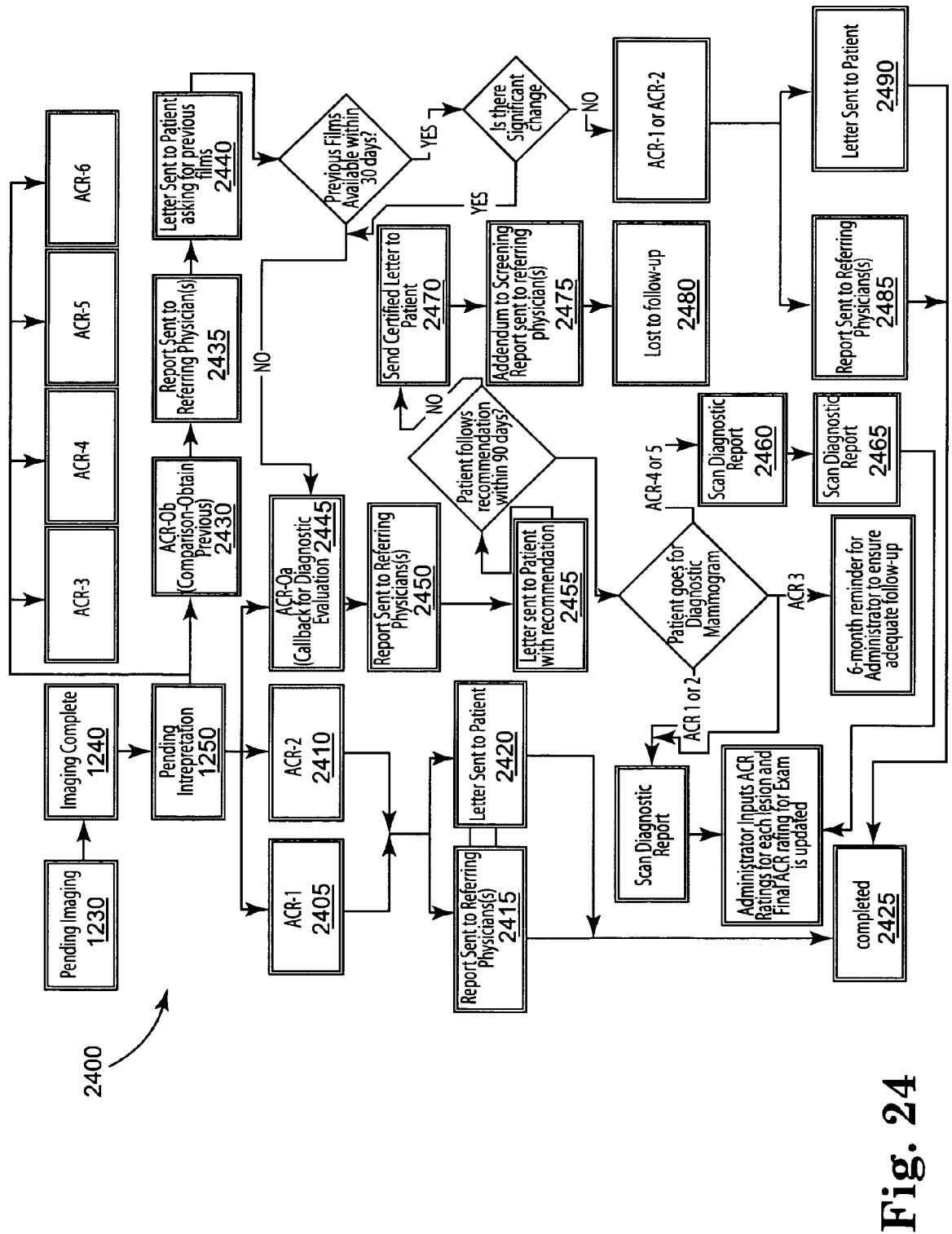
FIG. 24 is a flow diagram that describes steps in a method for a screening exam workflow in accordance with one described embodiment.

The mammography management system follows a specific workflow for screen exams. FIG. 24 depicts a procedural flow chart 2400 of the screening exam workflow through one embodiment of the mammography management system. Table 1 below lists the various exam statuses and the corresponding condition required for the exam to be placed in the particular status as used throughout the screening exam workflow.

TABLE 1

| Exam Status | Description | ACR Value |
|---|---|---|
| Pending Imaging | Occurs when the exam is initially created by an Administrator and it is not an Analog Image exam type. | |
| Imaging Complete | Occurs when the system detects that the study is available in the PACS database. This is also the initial status for Analog Image exams. | |
| Pending Interpretation | Occurs when the exam is assigned to a Radiologist either by the automated scheduler or by a user. | |
| Negative | Occurs when a Radiologist signs the negative results for an exam. | 1 or 2 |
| Benign | Occurs when a Radiologist signs the benign results for an exam. | 1 or 2 |
| Callback | Occurs when a Radiologist signs Callback results for an exam. | 0A |
| Compare | Occurs when a Radiologist signs Compare results for an exam. | 0B |
| Waiting for Documents | Occurs when an Administrator has printed the letter for a Compare results exam. | 0B |
| Documents Received | Occurs when requested comparison images are scanned into the system. When a new Exam is created for a patient with a MODALITY = SCANNED, all the Exams for the patient in status Waiting for Documents are set to Documents Received | 0B |
| Send Certified Letter | All callback exams whose recommendations were not complied with by the patients within 90 days would show up as in the Send Certified Letter status for the Administrator. The administrator would click on the lost to follow-up tab and see the list of exams for which certified letters need to be sent. | 0A |

TABLE 1-continued

| Exam Status | Description | ACR Value |
|---|---|---|
| Lost to follow-up | Occurs when a Radiologist signs-off on a Callback exam that has been identified as 90 days with no reception of the final outcome reports. | 0 |
| Completed | Occurs after signoff once the letters have been printed to be mailed to the patients. The exam status becomes complete for ACR values 1 and 2. | 1/2/3/4/5/6 |
| Draft | Occurs when the Radiologist save exam results as Draft. | |
| Cancelled | Occurs when an Administrator cancels an exam. This is only available prior to the initial signoff. | |
| Technical Repeat | Occurs when the Radiologist select Technical Repeat for the exam results. | |
| Waiting Tech Repeat | Once the Administrator has printed the Technical Repeat letters, the status is changed to Waiting Tech Repeat and appears in the Compare Queue | |
| Tech Repeat Completed | Occurs when a new study arrives for a patient that also has an exam in Technical Repeat status. Once a new Exam is created for a patient with a EXAMTYPE = TECHNICAL REPEAT, all the Exams for the patient in status Waiting Tech Repeat are changed to Tech Repeat Completed | |
| Pending Pathology | Occurs when the Administrator presses the Save as Preliminary button on the Final Outcome screen. | |
| Documents Unobtainable | When a Compare exam waits in Compare status for 30 days, the system will detect that is should be change to a Callback exam. However, the system does not automatically do this, rather the system changes the Exam status to Documents Unobtainable and then displays the exam to the Radiologist's Pending Exam list | |

After interpretation by a radiologist, when an exam has negative results (i.e., ACR 1 or 2) (2405 or 2410) a negative exam workflow is followed after sign-off by the radiologist, including generating and sending an exam results letter 2420 and report 2415 to the patient and referring physician respectively. The exam is then completed 2425.

When an exam has a compare result (i.e., ACR-0b) 2430, a compare exam workflow is followed an after initial sign-off by the radiologist. The ratings ACR-0a and ACR-0b in the present invention both correspond to ACR-0 for the Bi-Rads ratings, which indicates further imaging is needed. The 0a and 0b ratings are used in the present invention to convey more information than that conveyed by the ACR-0 Bi-Rads rating; namely ACR-0a and ACR-0b discern between a compare result and callback result respectively because the two results yield different workflows. The exam is marked as "compare, possible abnormality" or "compare, essentially normal" by the radiologist on the "exam results" page, and a report is sent 2435 and a letter is generated 2440 for the patient requesting that the previous films be sent to the facility where the original compare exam was performed. Next, the exam status is set to "compare" and the exam is listed in the "pending patient letters" list. When an administrator prints the letter, the exam status is changed to "waiting for documents," and the exam is listed in the "compare exams" list of the radiologist who indicated the need for comparison, which is typically the individual who completed the results page. Then, the exam is removed from the radiologist's pending exams list.

Upon arrival of the requested images at the facility, an administrator scans the images and enters into the mammography management system the patient ID via an acquisition station. The scanned images are electronically transmitted to the PACS database via the mammography management system server as a separate study with a unique DICOM study ID. The mammography management system utilizes the patient ID and to search for any existing exams related to the patient with the status of "waiting for documents." If such an exam is found the mammography management system takes the following steps: (1) create a new historic exam using the information from the DICOM header and relate the exam to the patient ID, (2) set the status of the existing "waiting for documents" exam to "documents received," (3) display on the "pending exams list" any exams with either the "pending interpretation" and "documents received" status, (4) remove the exam from the "compare exams" list, (5) receive final results of comparison (e.g., ACR 1 or 2) from radiologist, and (6) generate and mail/fax the exam compare results letter 2490 and report 2485. The exam is then completed 2425.

When the radiologist clicks the "results" link related to an exam with a "documents received" status from the "pending exams" list, the "exam results" page is displayed to the radiologist. The exam history is then displayed to the radiologist to see the newly created historic exam that contains the requested comparison images. If desired, the radiologist may select "callback, comparison completed" as the result for a compare exam. Upon this selection, the compare exam becomes a callback exam 2445 and continues forward with the callback exam workflow described in more detail below.

When an exam has callback results (i.e., ACR-0a) 2445 a callback exam workflow is followed after sign-off. First, the exam status is changed to "callback," and a callback letter 2455 and report 2450 are generated and faxed to the patient and the referring physician respectively. Then, the exam is listed in the callback exam list. The callback results letter is printed and mailed, and reminder letters are sent at 30 and 60 day intervals if final outcome is not entered. If the patient undergoes the diagnostic exam, as described in more detail below, the diagnostic 2460 and pathology 2465 reports are received and scanned, and the administrator or lead interpreting physician enters the final outcome, at which point the exam is completed 2425. If the final outcome is not entered into the mammography management system within 90 days, the exam moves to the "lost to follow up" process 2480.

More specifically, when a callback exam is 90 day past due, the "lost to follow up" exam workflow 2470 ensues, which is initiated when the mammography management system detects that an exam in callback status is 90 days past creation date. The exam is displayed on the administrator's "lost to follow up" list and is removed from the callback exam list. The system generates the lost to follow up patient letter 2470, and the administrator prints and mails the lost to follow up letter. The exam is moved to the pending exams list for the radiologist that provided the original results, and the radiologist may electrically sign the report, thereby resulting in the mammography management system generating 2475 the lost to follow up report for all relevant physicians. The exam status is then changed from callback to lost to follow up 2480.

When an exam is technically inadequate, an exam repeat is required, called a technical repeat. The technical repeat exam workflow begins when an exam status is saved as "technical repeat." The technical repeat letter and report are generated and faxed, and the exam results letter is printed. Next, the status of the exam is changed to "waiting tech repeat," and the exam now appears in the "compare exam" list. The patient then returns for a repeat of the exam, and the new study images are transfer to PACS. The PACS trigger creates a new exam as a placeholder for the images with a status of "complete." The PACS trigger also updates the status of the original exam from "waiting tech repeat to "tech repeat completed." The original exam is moved from the radiologist's "compare/repeat exam" list to the radiologist's "pending exam" list. Next, the radiologist enters the final results, and the exam results letter and report are generated and faxed. The exam results letter is printed, and the exam is completed.

Figure 25:
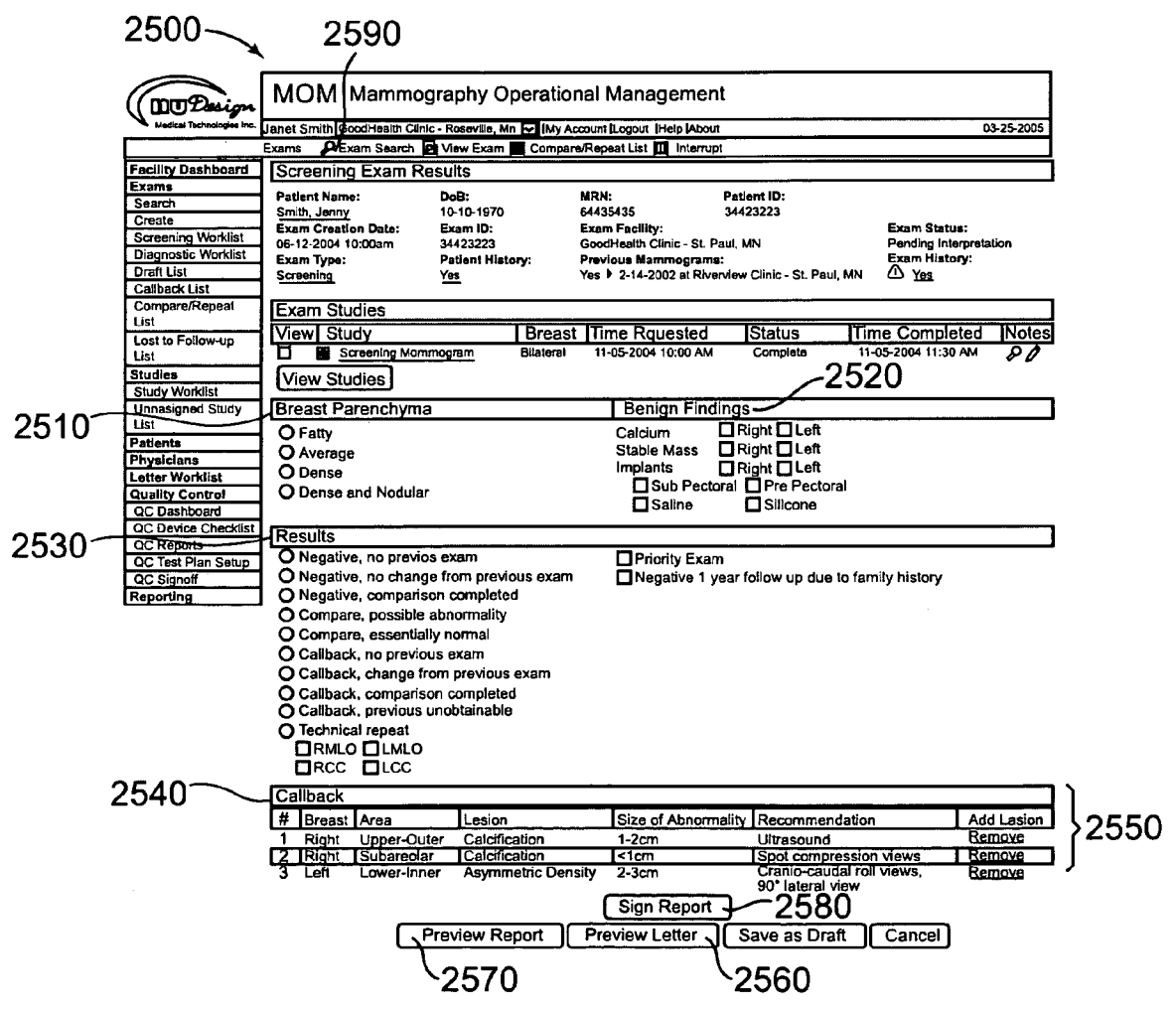

As described, upon viewing and analyzing a screening exam the radiologist enters the results of a mammography screening into an "exam results" screen of the mammography management system. An example of the "exam results" screen 2500 is seen in FIG. 25. When the "exam results" screen 2500 is loaded, the current study images as well as the last two historical exam study images for the patient are downloaded from PACS to appropriate viewing software if the images are not already cached.

From the "exam results" screen 2500, the radiologist has access to information relating to the patient, relevant patient history, previous exams associated with the patient that are stored in the mammography management system, and other information that may be useful to the radiologist during review of the current exam results. Access in the system to additional patient exams allows the radiologist to view the previous exam results for purposes of comparison with the current results.

When the radiologist is prepared to enter screening exam results in to the mammography management system, he or she may again interact with the "exam results" screen 2500. Under the "breast parenchyma" heading 2510, the radiologist can choose from the following options to reflect the exam results: fatty, average, dense, and dense and nodular. The default value for this option is average. Under the "benign findings" heading 2520, the radiologist may select whether any of the options—calcium, stable mass or implants—are present on the left breast, the right breast, or both. If the radiologist selects the implants option, he or she may further select one or more of the options: sub pectoral, pre pectoral, saline and silicone.

Under the "results" heading 2530, the radiologist may select from the following options: "negative, no previous exam," "negative, no change from previous exam," "compare, possible abnormality," "compare, essentially normal," "callback, no previous exam," "technical repeat," and "callback, change from previous exam." Table 2 below lists the various screening result options and indicates when they are available for selection to the radiologist user.

TABLE 2

| Result | Description | Available |
| --- | --- | --- |
| Negative, no previous exam | No previous exams, no need to compare (ACR 1 or 2) | Initial Result or Tech Repeat Complete |
| Negative, no change from previous exam | Previous exam (already in system) reviewed, no change (ACR 1 or 2) | Initial Result or Tech Repeat Complete |
| Negative, comparison completed | After requested documents received and Radiologist reviewed (ACR 1 or 2) | Comparison Result |
| Compare, Possible Abnormality | System does not contain previous exam, Radiologist requests (ACR Ob) | Initial Result or Tech Repeat Complete |
| Compare, Essentially Normal | System does not contain previous exam, Radiologist requests (ACR Ob) | Initial Result or Tech Repeat Complete |

TABLE 2-continued

| Result | Description | Available |
| --- | --- | --- |
| Callback, no previous exam | No previous exams, require callback (ACR 0a) | Initial Result or Tech Repeat Complete |
| Callback, change from previous exam | Previous exam (already in system) reviewed, and change detected (ACR 0a) | Initial Result or Tech Repeat Complete |
| Callback, comparison completed | Initially was a Compare to previous exam, documents received, more studies needed (ACR 0a) | Comparison Result |
| Callback, previous unobtainable | Could not get previous exams, further studies needed (ACR 0a) | Comparison Result (only when timeout waiting for documents) |
| Technical Repeat | Exam technically inadequate, repeat views required | Initial Result or Tech Repeat Complete |

If the radiologist selects the result "negative, no previous exam" or "negative, no change from previous exam" under the "results" heading 2530 and one of the options under the "breast parenchyma" heading 2510 is selected, the ACR rating is automatically set to 1. If the radiologist selects the result "negative, no previous exam" or "negative, no change from previous exam" under the "results" heading 2530 and either "calcium" or "stable mass" are selected under the "benign findings" heading 2520, the ACR rating is automatically set to 2. If the radiologist selects the result "callback, no previous exam" under the "results" heading 2530, the ACR rating is automatically set to 0a. If the radiologist selects the result "compare, possible abnormality" or "compare, essentially normal" under the "results" heading 2530, the ACR rating is automatically set to 0b.

If the images obtained are blurry, the radiologist selects the result, "technical repeat." The user can subsequently select one or more of the options RMLO, LMLO, RCC, and LCC, to indicate which of the images are not technically sufficient for reading. Upon signing the report with a "technical repeat" result, the exam status is updated as "technical repeat" and a letter is generated and sent to the patient.

The radiologist can also indicate in the mammography management system when the exam is a priority exam by checking the "priority exam" check box under the "results" heading 2530. Additionally, even for patients younger than 40 years, if the patient has a family history of cancer the radiologist can specify that the patient needs to undergo annual mammograms by checking the check box "negative 1 year follow up due to family history" check box under the "results" heading 2530.

If any of the "callback" or "compare" results are selected by the radiologist-user, the radiologist is provided a user interface into which to enter and identify an area and type of abnormality. In one embodiment seen in FIG. 26, an "add lesion" popup window 2600 is automatically displayed to the radiologist responsive to selection of a "callback" or "compare" result. The popup window can also be displayed manually responsive to the radiologist pressing the "add" button 2610 on the "add lesion" popup window 2600. As shown in FIG. 26, the radiologist may select a plurality of radio buttons specifying the left breast or the right breast, as well as the area of the breast (e.g., upper-outer, upper-inner, lower-outer, lower-inner, subareolar and axilla) where the abnormality is observed. Radio buttons are provided in each quadrant of the breast diagram to mark the type of abnormality (i.e. calcification, mass, asymmetric density, or architectural distortion). The radiologist can also indicate the size of the abnormality and one or more recommendations by selecting the appropriate corresponding radio button or check box. Pressing the "add" button 2610 saves the entered lesion and clears the "add lesion" popup window for a new lesion entry. Pressing the "finish" button 2620 with no fields populated saves any previously entered lesions and closes the popup window 2600.

Lesions that are thereby entered by the radiologist are populated into the "lesion table" 2550 in the "callback" section 2540 of the "exam results" screen 2500 with a row listing the breast, area, lesion, size of abnormality, and recommendations provided by the radiologist. The lesions are listed on the "lesion table" 2550 in the order they were entered.

Again with reference to FIG. 25, when the radiologist has completed entering the lesion information, he or she may select the "preview letter" button 2560, thereby causing a pop-up screen containing a preview of the letter that will be sent to the patient. An example of such a letter 2700 is shown in FIG. 27, which includes an electronic signature box 2710 for the radiologist to sign. When the radiologist has completed entering the lesion information, he or she may also select the "preview report" button 2570, thereby causing a pop-up screen containing a preview of the report that will be sent to the referring physician. An example of such a report 2800 is shown in FIG. 28, which also includes an electronic signature box 2810 for the radiologist to sign.

As seen in FIG. 27, patient letters may include a recommended time for the next exam. A set of rules may be used to determine the recommended time for the next exam. For example, in one embodiment, the set of rules is as follows. If "negative 1 year follow up due to family history" is checked then the letter includes the following recommendation: "I therefore recommend that you have another mammogram in one year based on your family history of breast cancer." Otherwise, if the patient's age is less than 40, then the letter includes the following recommendation: "I therefore recommend that you have another mammogram at age 40." Otherwise, if the patient's age is 40 or greater, then the letter includes the following recommendation: "I therefore recommend that you have another mammogram in one year."

Both the letter and report are editable by the radiologist, such that the radiologist can make and save changes if desired. Upon completion of reviewing the report and letter, the radiologist selects the "sign report" button 2580 on the "exam results" screen 2500, which adds the radiologist's signature to the report and letter and moves the workflow to the next step, which typically includes printing of the letter.

Figure 29:
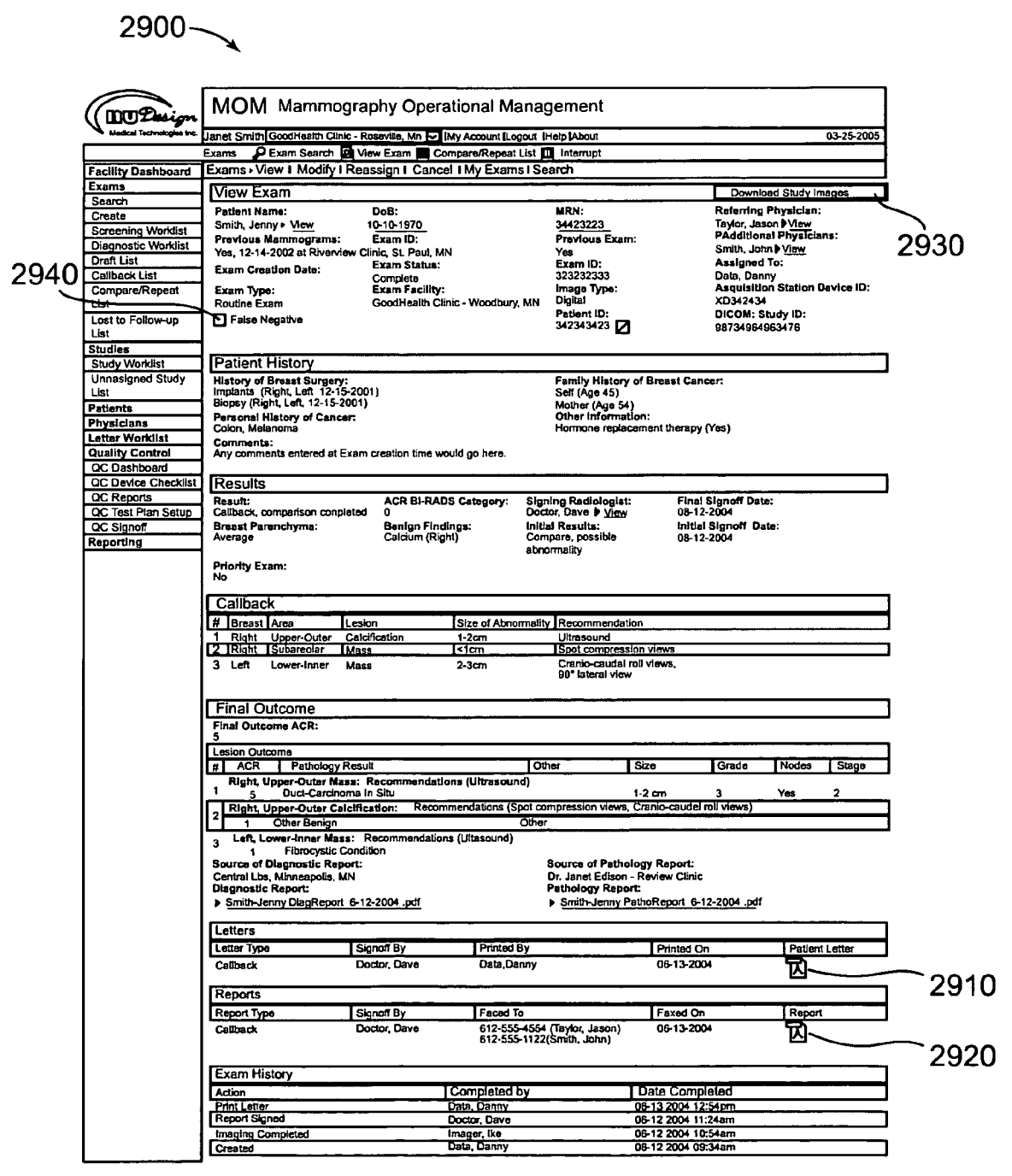

Upon completion of the above exam result entry steps, selection of the "view" button 2590 displays to the user the entered details of an exam 2900 in read-only format as seen in FIG. 29. All of the information seen in the "view exam" screen 2900 is displayed to the user. Additionally, the letter and report generated by the radiologist are viewable by selecting the corresponding icons 2910 and 2920 respectively. Furthermore, the lead interpreting physician, radiologists, and referring physicians with appropriate permissions to the mammography management system may select the "download study images" button 2930 shown in the upper toolbar, responsive to which the study images associated with the exam are downloaded to the viewing software. The "false negative" checkbox 2940 is available to the lead interpreting physician and is used to indicate if an exam was falsely screened as a negative.

Diagnostic Exams

Figure 30:
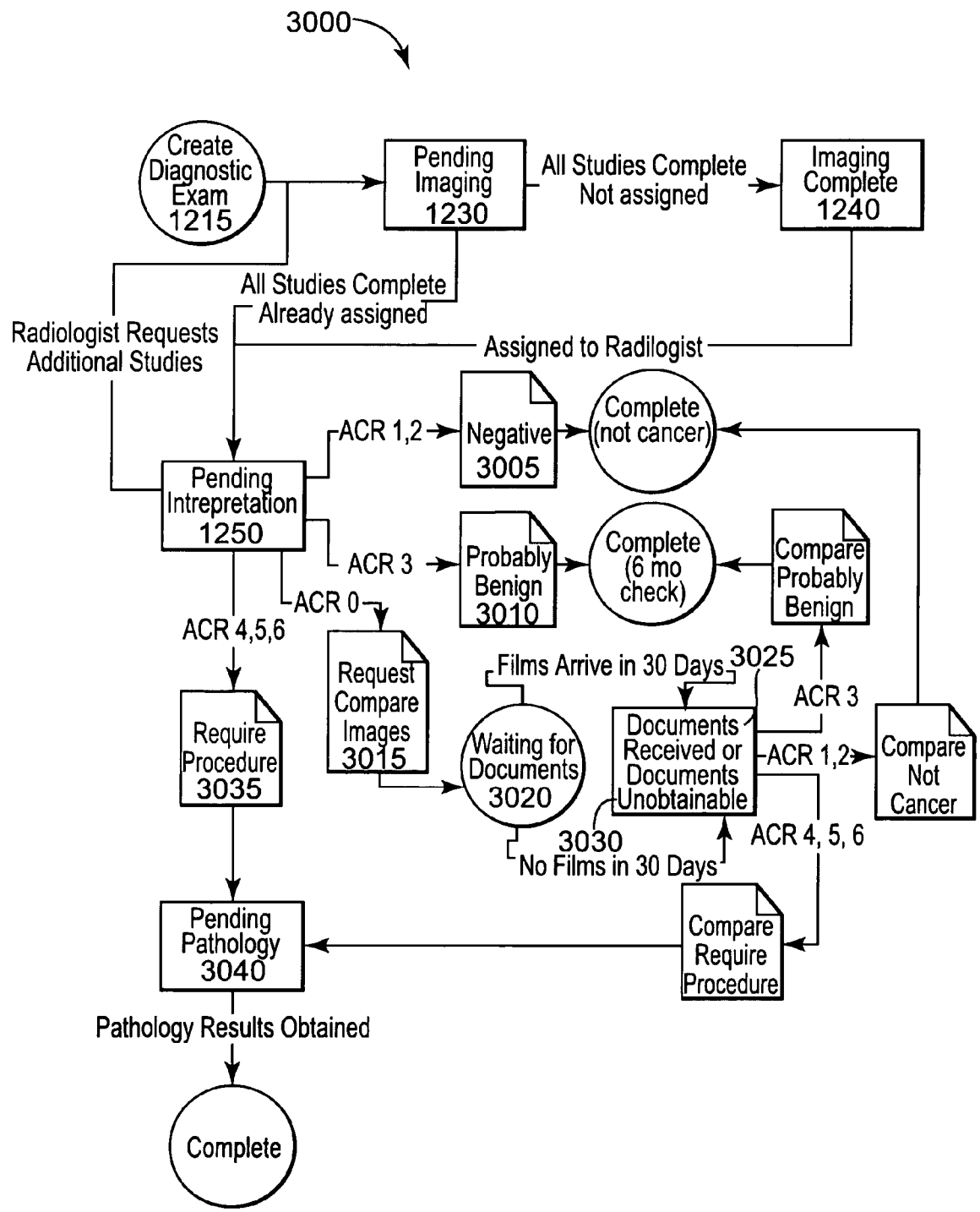
FIG. 30 is a flow diagram that describes steps in a method for a diagnostic exam workflow in accordance with one described embodiment.

When a screening exam uncovers an abnormality, the exam is recorded and stored in the mammography management system as a "callback" result. The patient is then requested to obtain a subsequent diagnostic exam. FIG. 30 depicts a procedural flow chart 3000 of the diagnostic exam workflow through one embodiment of the mammography management system. As result of a diagnostic exam, an additional procedural exam such as a biopsy may subsequently be required. Procedural exams are also supported by the mammography management system, as described in more detail below. By managing all such exams jointly in the mammography management system, the exams are logically linked together in the system and the final outcome data from the exams is stored and maintained in a single logical location by the mammography management system. The statuses that can be assigned to a diagnostic exam throughout the diagnostic exam workflow are the same statuses described above with respect to the screening exam workflow.

When the patient arrives at the exam facility 1210, the patient typically registers at the front desk and fills out the necessary paperwork, such as insurance forms. Next, the technologist or administrator interviews patient and creates a diagnostic exam in the mammography management system at step 1215. Creating the exam within the system requires entry of the reason for the diagnostic exam (e.g., lump in breast or pain in breast), entry or update of the patient history, and selection of the initial type of imaging study.

If no studies were requested at the time the diagnostic exam was created, the exam is assigned a "pending imaging" status 1230 because at least one study is required prior to review by a radiologist. The exam then is displayed in a special list of exams with no requested/completed studies that is located on the "technologist dashboard" screen described below. The technologist is thereby informed that the patient is waiting and that the technologist will need to use the "modify exam" screen to request the initial study.

If studies are requested at the time the diagnostic exam is created, the exam is assigned a "pending imaging" status 1230. Each requested study is displayed in a "study worklist" for the facility. When all outstanding requested studies are completed 1240, the exam assigned to a radiologist, is set to "pending interpretation" status 1250, and moved to the assigned radiologist's queue. If no radiologist is assigned, the exam is displayed in the "pending interpretation" queue for any radiologist that is monitoring the facility. The mammography management system provides the radiologists to ability to assign such exams to themselves.

When the technologist is preparing to perform the requested study (e.g., diagnostic mammogram, sonogram, or MRI), the study is pushed from modality to PACS, wherein the DICOM images are transferred from the acquisition device (e.g., x-ray machine in the case of a mammogram, ultrasound machine in the case of a sonogram, and a magnetic machine in the case of an MRI) to PACS, and the mammography management system receives the notification and creates a study reference to the exam/patient. Upon completion of the study, the technologist enters the study completion data, and the exam is then moved to radiologist's worklist.

Next, the radiologist reviews study and examines patient. Correspondingly, the radiologist opens the "exam results" page in the mammography management system to review patient information and the initial study. Typically, the study is received from the modality on the soft copy review station (SCW), but in some scenarios the initial study may be received from the PACS. Prior to final signoff the radiologist can request an additional study. When this occurs the exam is assigned the "pending imaging" status. Each requested study is placed in the "study worklist" for the facility and is removed from the radiologist's worklist while waiting for the imaging to complete.

If additional studies are requested, the technologist reviews "study worklist" and performs the additional requested study. Accordingly, the study is pushed from modality to PACS, and the mammography management system receives the notification and creates a study reference to the exam/patient. Upon completion of the additional study, the technologist enters the study completion data, and the exam is set to "pending interpretation" status and moved to the radiologist's worklist.

Next, the radiologist reviews the study images and determines the results. To review the study images, the radiologist opens the "exam results" screen in the mammography management system and views a listing or all the studies received from PACS. The radiologist views the study images and enters the lesions into the mammography management system as previously described with respect to the screening exam.

Finally, the radiologist signs off on the exam results as previously described with respect to the screening exam. To sign off, the radiologist presses the "sign report" button 3110 seen in FIG. 31, in response to which the mammography management system generates the patient letter and physician reports. The letter is generated to reflect the ACR value assigned based on the radiologist's review of the images as described below. If a related screening exam existed for the patient in the mammography management system, the ACR values on the final outcome are automatically populated.

When the radiologist signs the results for a diagnostic exam in the mammography management system, the system automatically calculates the initial ACR. If the ACR is 1 or 2 (block 3005) or 3 (block 3010) the exam is considered negative. After the letter is printed the exam is set as completed.

When the radiologist requests previous studies for comparison (ACR 0) (block 3015) the exam is considered a "compare" exam. After the letter is generated for the patient instructing her to provide the previous images, the exam status is set to "waiting for documents" (block 3020). If the images are obtain within 30 days they are scanned and added to the exam as a study, and the exam is set to "documents received" status (block 3025) and added back into the radiologist's "pending interpretation" worklist for final results. If the images are not received within 30 days the exam is set to "images unobtainable" status (block 3030) and still added back in the radiologist's "pending interpretation" worklist for final results. When the letters are generated in the mammography management system for the final results of a compare exam, the letter indicates whether the requested images were or were not received and reviewed.

When the radiologist enters lesions for a diagnostic exam the ACR is calculated by taking the highest ACR value on all the lesions. If this value is a 4, 5 or 6 (block 3035) a further procedure is required. The letter sent to the patient informs her of the need to obtain the procedure. If the patient is in-clinic and the procedure is performed the same day a letter will still be sent for compliance. The exam is then set to "pending pathology" status (block 3040). When the pathology outcome is entered into the mammography management system, either by system update from the related procedure exam or manually, the exam is considered complete.

Figure 31:
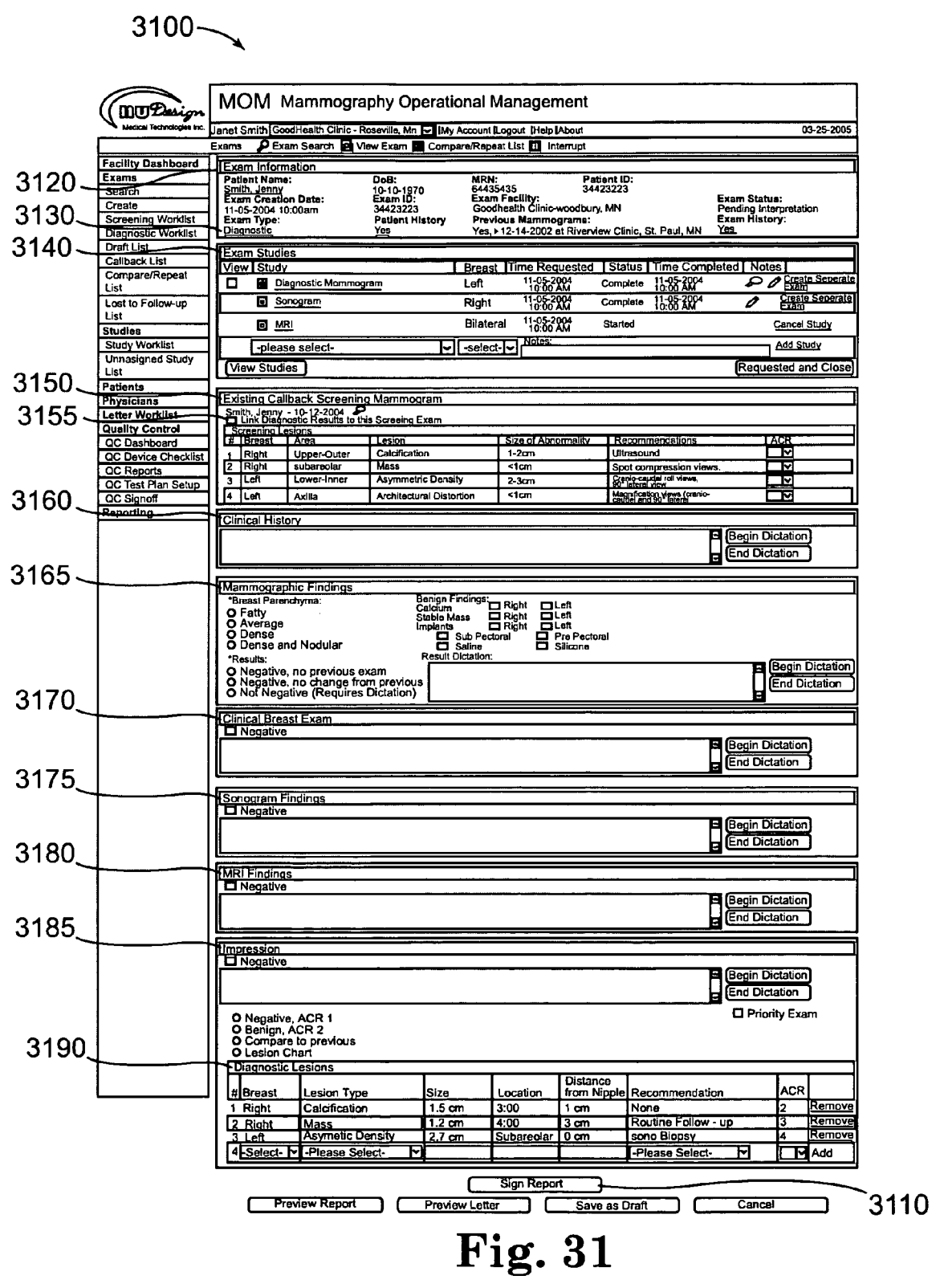

With reference to FIG. 31, the diagnostic exam results screen 3100 is utilized by the radiologist to review patient history and previous exams, to view study images associated with the patient and request new studies, to record the final outcome ACR for related screening exams, and to enter the study results and impressions for the diagnostic exam.

Figure 32:
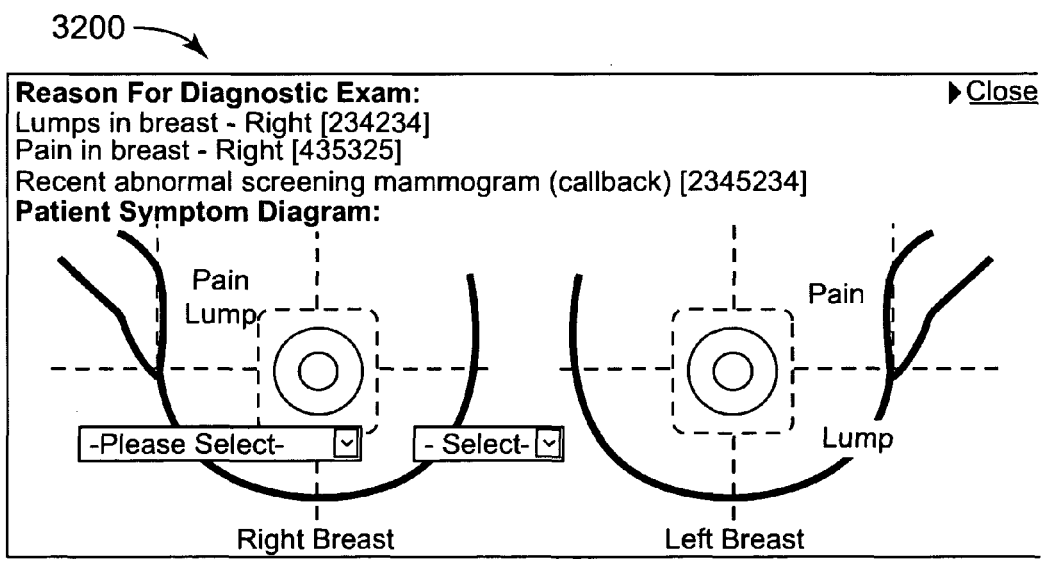
FIG. 32 is a diagram of an exemplary user interface for a patient symptom diagram screen in accordance with one specific implementation.

The "exam information" section 3120 of the diagnostic exam results displays relevant patient and exam information including details of the diagnostic exam, patient history, and exam history. Clicking the link 3130 under "exam type" opens a popup window that display all the reason for the diagnostic exam, selections that where made on the "exam creation" screen, and the patient symptom diagram. This display 3200 is shown in FIG. 32.

The "exam studies" section 3140 of the diagnostic exam results screen 3100 lists all image studies received from various modalities. The requested but unfulfilled studies are also displayed in this section. The radiologist may request new studies and cancel studies in requested status in the "exam studies" section 3140. If a study is available in the mammography management system in digital format it is viewable by selecting the view icon that, when clicked, opens a "view study" screen in a popup window.

If an open callback screening exam (i.e., screening exam in "callback" status) exists for the patient in the mammography management system then the "existing callback screening mammogram" section 3150 is displayed, as seen in FIG. 31.

The "link diagnostic results to this screening exam" checkbox 3155 causes the screening lesions table to be displayed. Linking the diagnostic results in requires the radiologist to enter the ACR value for the screening exam final outcome. The ACR values entered in this section are stored just as if a user were to add the final outcome for the screening exam using the existing interfaces in the mammography management system. If the exams are linked when the radiologist presses the "sign report" button 3110 on the diagnostic exam results screen 3100, the ACR values are populated to the linked screening exam's final outcome. If the diagnostic exam's ACR value is 1, 2 of 3, the related screening exam's final outcome is set as complete and no further pathology results are required. After the screening exam's final outcome ACR values are updated, the related screening exam status is then set to "complete."

The "clinical history" section 3160 of the diagnostic exam results screen seen in FIG. 31 includes a text area where the radiologist can type or dictate freeform text any additional relevant clinical history information.

The "mammographic findings" section 3165 of the diagnostic exam results screen is only displayed if a fulfilled study of type "diagnostic mammogram" is associated with the exam. The "mammographic findings" section 3165 allows the radiologist to enter breast parenchyma, benign findings, and other results for the diagnostic mammogram study. These findings are previously described with respect to the screening exam above.

The "clinical breast exam" section 3170 of the exam results screen includes a textbox editable by radiologist to include findings from a physical examination. The "sonogram findings" section 3175 is only displayed if a fulfilled study of type sonogram is associated with the exam and includes a textbox editable by the radiologist to include findings from the sonogram study and a "negative" checkbox to indicate negative results. The "MRI findings" section 3180 is only displayed if a fulfilled study of type MRI is associated with the exam and includes a textbox editable by the radiologist to include findings from the MRI study and a "negative" checkbox to indicate negative results.

The "impression" section 3185 allows the radiologist to enter the overall exam results, the diagnostic lesions, and freeform dictation. The radiologist must select one of the following overall results: Negative, ACR 1; Benign, ACR 2; Probably Benign, ACR 3; Lesion Chart. The entries in the "impression" section 3185 are used by the mammography management system to determine the body of the letter and report for the diagnostic exam. Finally, the "diagnostic lesions" section 3190 of the exam results screen includes a table into which the radiologist enters lesions identified during the diagnostic exam.

Figure 33:
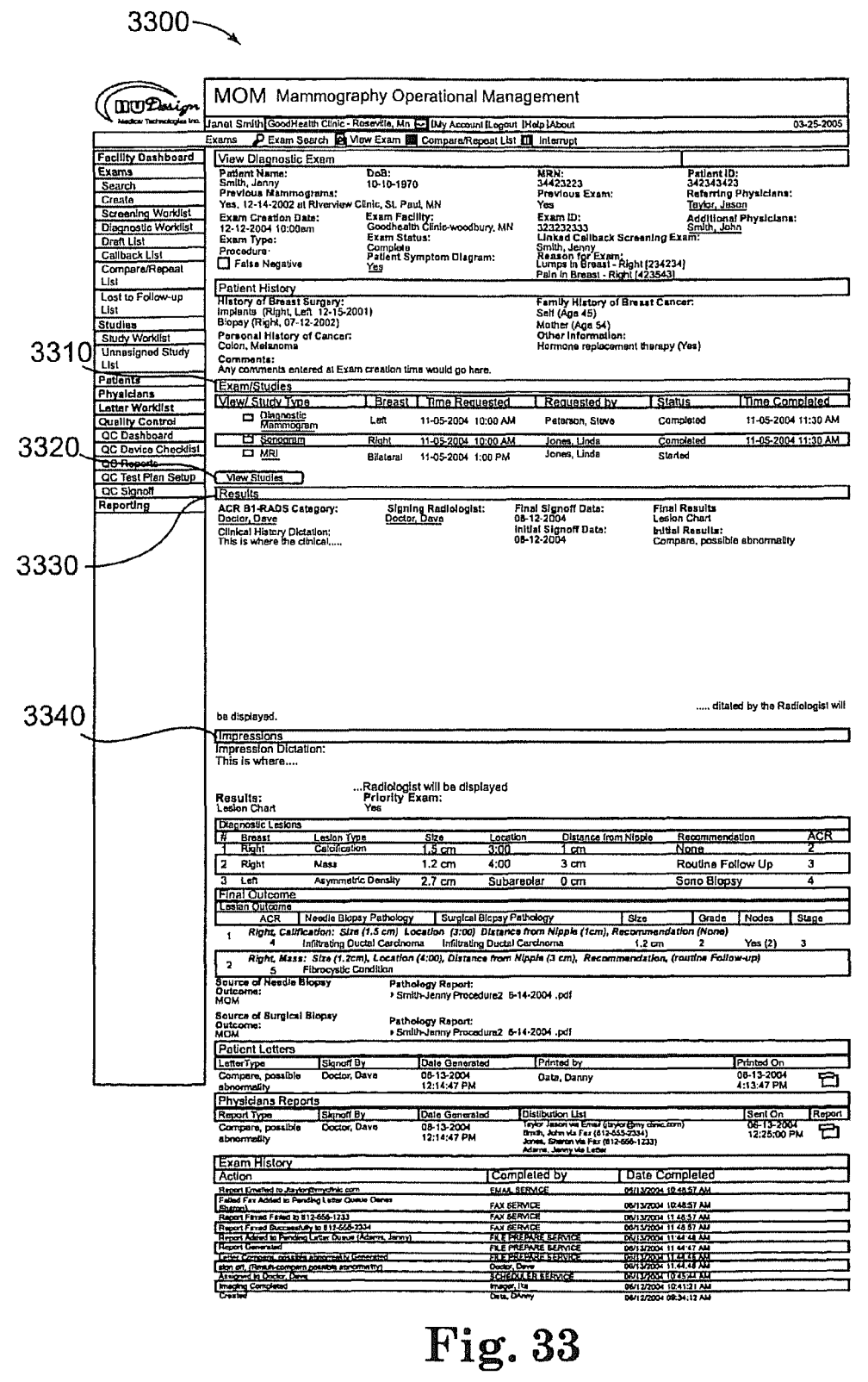

The "view diagnostic exam" screen is displayed when a user selects to view a diagnostic type exam. FIG. 33 shows a "view diagnostic exam" screen 3300 in accordance with one embodiment of the present invention. Portions of the information displayed on the screen are substantially similar to the "view screening exam" screen. The "exam studies" section 3310 includes a "view studies" button 3320, the selection of which causes the display of the a selected study. Additionally, the "view diagnostic exam" screen 3300 includes further written description of the results 3330, and the impression 3340 as seen in FIG. 33.

Procedure Exams

Figure 34:
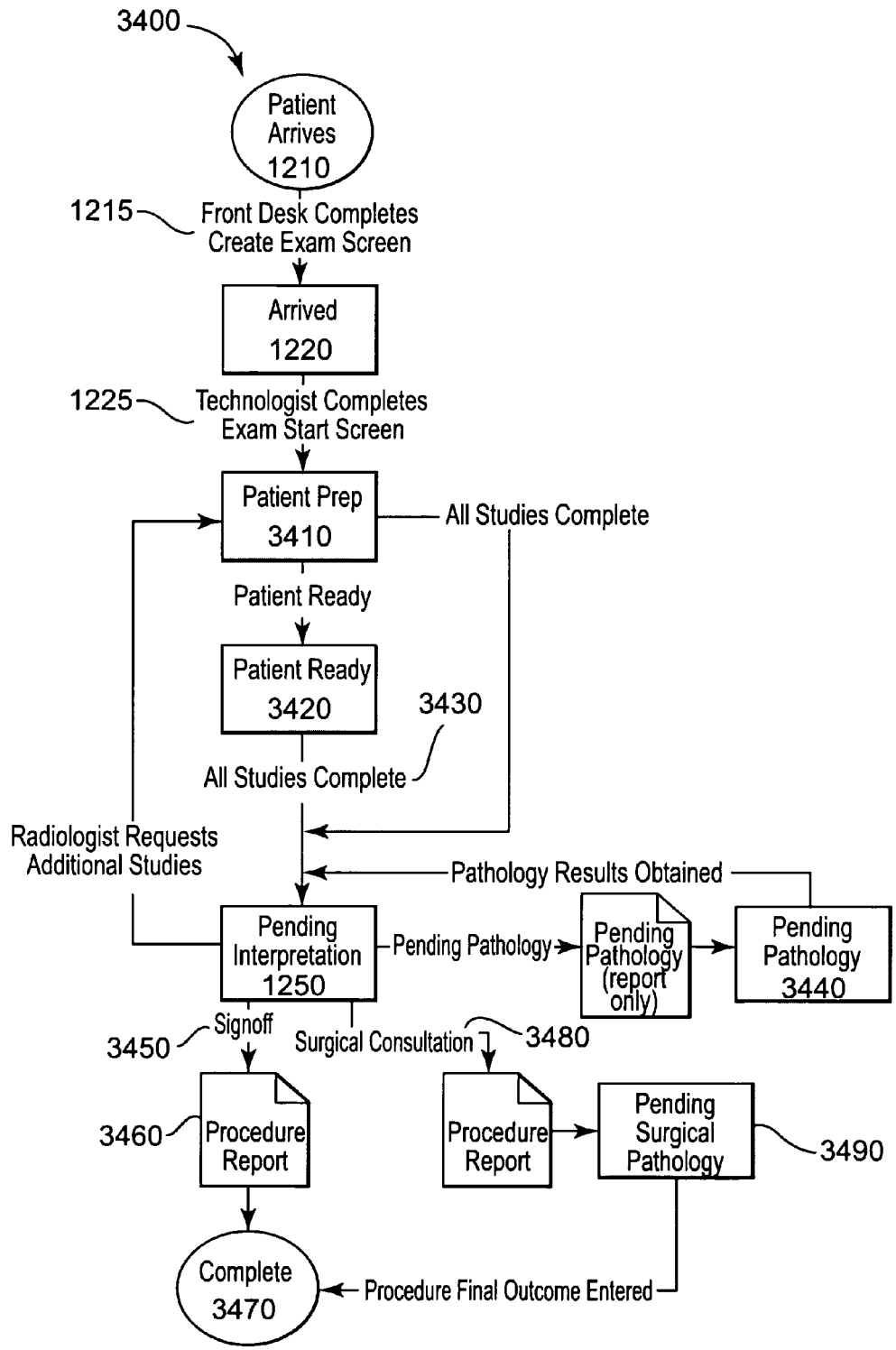
FIG. 34 is a flow diagram that describes steps in a method for a procedural exam workflow in accordance with one described embodiment.

A result of a diagnostic exam, an additional procedural exam may be required. FIG. 34 depicts a procedural flow chart 3400 of the procedural exam workflow followed at the facility where the exam is performed through one embodiment of the mammography management system. Table 3 below lists the various exam statuses and the corresponding condition required for the exam to be placed in the particular status as used throughout the procedure exam workflow.

TABLE 3

| Exam Status | Description |
| --- | --- |
| Arrived | Occurs when the patient arrives at the facility and is checked in by the admissions staff. This is the first half of the new two-step exam process. |
| Patient Prep | For Procedure exams the Patient Prep status occurs after the Start Exam screen is completed by a Technologist. In order for this to occur at least on study must be requested by the Technologist. The Patient Prep status indicates that the patient is being prepared for the study. The Patient Prep status also occurs when a new study is requested by the Radiologist from the Procedure Exam Results screen. |
| Patient Ready | For Procedure exams the optional Patient Ready status occurs when a Technologist indicates that the Patient has been prepared for the Radiologist to perform the study. However, the study may be started and completed by the Technologist without indicating that the patient is ready (if the Radiologist is not required to perform the study). |
| Pending Interpretation | After studies have been completed the status is set to Pending Interpretation. |
| Pending Pathology | Occurs when the Radiologist checks the Pending Pathology checkbox on the Procedure Exam Results screen. |
| Pending Surgical Pathology | Occurs when the Radiologist selects the Surgical Consultation as a Recommendation on the Procedure Exam Results screen. This indicates that the patient requires surgery and the exam will be held in the Pending Surgical Pathology until the surgical pathology results are entered on the Procedure Final Outcome screen. While in Pending Surgical Pathology status the exam will be listed on the Final Outcome List for the facility. |
| Cancelled | Occurs when an Administrator cancels an exam. This is only available prior to the initial signoff. |
| Completed | Occurs after signoff if a Surgical Consultation is not recommended. |
| Draft | Occurs when the Radiologist pressed the Save As Draft button on the Diagnostic Results screen. |

Initially, the patient arrives at the facility (step 1210) and registers with admissions (step 1215). Demographic and insurance information is collected from the patient and entered into the "start exam" screen, and the patient is presented with the disclosure for signature, both as previously described. The exam is initially created in the mammography management system with an "arrived" status 1220. The technologist interviews patient and completes the "start exam" screen (step 1225) in the mammography management system as previously described by entering the reason for procedure exam (e.g., lump in breast, pain in breast, etc), updating patient history as necessary, and selecting the initial type of study.

Upon completion of the "start exam" screen, the exam status is set to "patient prep" status 3410 and the corresponding study request is added to the study worklost for the facility. The technologist then prepares the patient in the room for the requested procedure, and a radiologist is assigned to the exam if one is not already assigned. The technologist then sets the exam status in the mammography management system to "patient ready" status 3420. The exam is not added to the radiologist's exam worklist until the status is set to "patient ready."

The exam is now listed on the assigned radiologist's exam worklist as ready for the procedure. The radiologist and technologist then perform and complete the requested study/procedure. Upon completion of the study/procedure, the study completion data is entered into the mammography management system, typically by the technologist. The, the study is marked as "completed" 3430 in the mammography management system. The exam is then moved in the system moved to the radiologist's exam worklist with a status of "pending interpretation" 1250.

The radiologist reviews exams based on the procedure performed by opening the corresponding procedure exam results page in the mammography management system from the exam worklist. If necessary, the radiologist may request an additional study for more procedures or to take images by adding the request to the study worklist in the mammography management system for the facility. If the radiologist adds an additional request, the study is removed from the radiologist's worklist while waiting for the imaging to complete, and the exam status is set back to "patient prep" 3410.

The technologist reviews study worklist and performs and completes the additionally requested study. The study is pushed from modality to PACS in the mammography management system, and the system receives the notification and creates a study reference to the exam/patient. Technologist then enters the study completion data into the mammography management system. The exam is then moved in the system to the radiologist's worklist with the status of "pending interpretation."

The radiologist reviews the study images, and enters findings, results and recommendations by opening the procedure exam results and viewing a listing or all the studies received by from PACS . The radiologist views the study images with a software viewer, and records the findings and the lesions results in the mammography management system. When a procedure is performed, the resultant specimen may need further pathology work to be performed to determine the outcome. In such a scenario, the radiologist may still dictate the exam results, but keep the exam in "pending pathology" status 3440 while waiting for the final pathology outcome.

Figure 35:
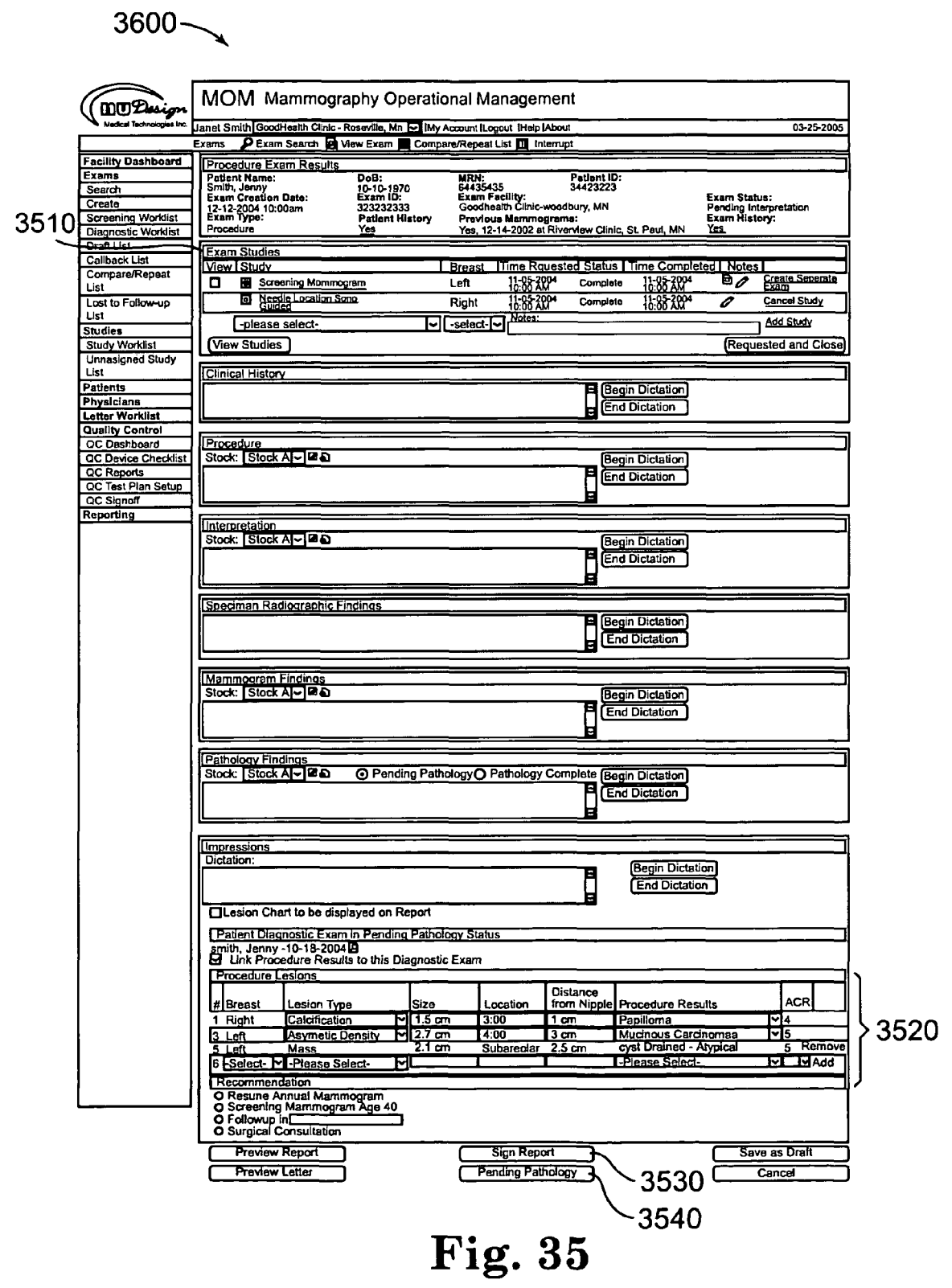

The "procedure exam results" screen is utilized by the radiologist to review patient history including previous exams recorded in the mammography management system, to view study images associated with the exam and request new studies, to enter the study findings and impressions for the exam, and to record lesion procedure results and a exam recommendation. An example of a "procedure exam results" screen 3500 in accordance with one embodiment of the present invention is shown in FIG. 35. The interface of the "procedure exam results" screen 3500 functions substantially similarly as the "diagnostic exam results" screen described above. One difference is seen in the "exam studies" section 3510, where different types of studies may be requested as seen in FIG. 35. Additionally, all lesions from the linked diagnostic exam with an ACR value of 4, 5, or 6 are automatically populated into the "procedure lesions" table 3520.

Moreover, the procedure exam final outcome screen is used for entry of the surgical pathology final outcome of a procedure exam that is in the "pending pathology" status 3440. Each lesion that is indicated as a carcinoma on the "procedure lesions" table 3520 is displayed in the final outcome section. A surgical pathology is required to be entered for these lesions, and the surgical pathology contains the details of the cancer as documented during the actual surgery, versus a biopsy.

Upon completion of the radiologist's review of the study images, the radiologist signs off 3450 on the exam results by selecting the "sign report" button 3530 on the "procedure exam results" screen 3500, responsive to which the mammography management system generates the physician reports 3460. The exam is then set to the "completed" status 3470. Procedure exams do not have an overall ACR value for the outcome in the mammography management system. Rather, they are classified into one of the following categories: negative, positive, or surgical consultation. If the radiologist is still waiting for the pathology work, he or she may select the "pending pathology" button 3540 on the "procedure exam results" screen 3500, which indicates that the final pathology has not yet been received.

When the radiologist does enter the final pathology results for a procedure, the radiologist also enters into the mammography management system an overall recommendation. If the recommendation is for a surgical consultation 3480, a report 3485 is generated for the associated physicians and the exam is set to "pending surgical pathology" status 3490. The exam remains in that status until the "procedure final outcome" screen 3500 is completed. Procedure exams in the "pending surgical pathology" status 3490 are listed on the "exam final outcome list," also called the "callback list" for the facility at which the exam was created.

Figure 36:
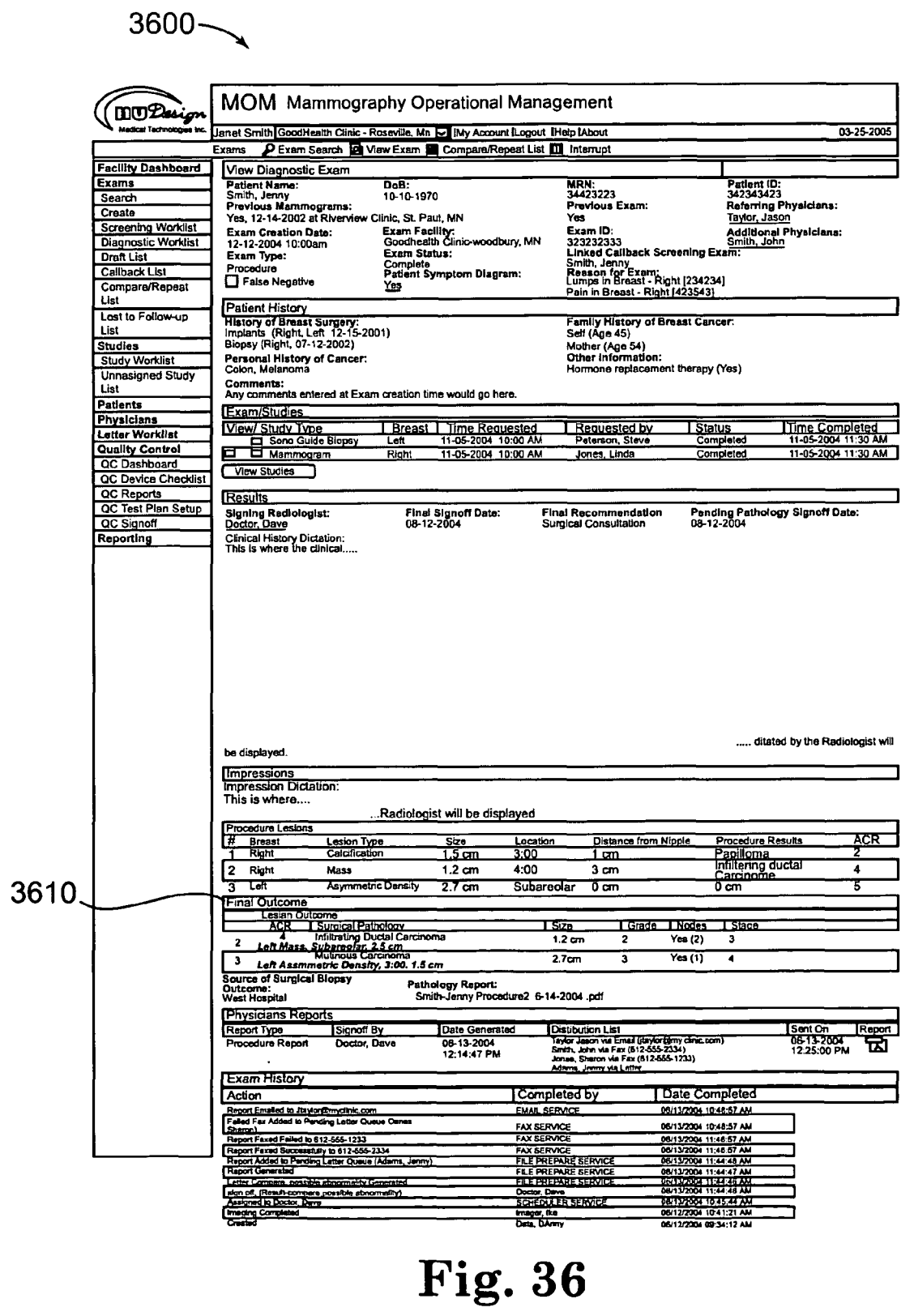

As with the other exams, a completed procedure exam can be viewed on the "view procedure exam" screen. An example of the screen 3600 in accordance with one embodiment of the present invention is seen in FIG. 36. The "final outcome" section 3610 of the screen displays the surgical pathology final outcome for the exam. Only an exam with the "surgical consultation" recommendation will have a "surgical pathology" final outcome. Accordingly, the "final outcome" section 3610 is only displayed if a final outcome exists for an exam in "completed" status 3470.

Inter-Exam Workflow

Again with reference to FIG. 11, the screening, diagnostic and procedure exams are interrelated. For example and as described above, a screening exam 1110 that yields an ACR 0 (callback) result requires that the patient return for a diagnostic exam 1120. A diagnostic exam 1120 that yields a final ACR of 4, 5, or 6 requires that a patient have a procedure 1130 performed. If the mammography management system is utilized to support all of these exams, the exams are logically linked by the system. A linked group of screening, diagnostic, and procedure exams are considered a series, and a lesion number within a linked exam series remains consistent throughout the different exams.

Figures 37, 38:
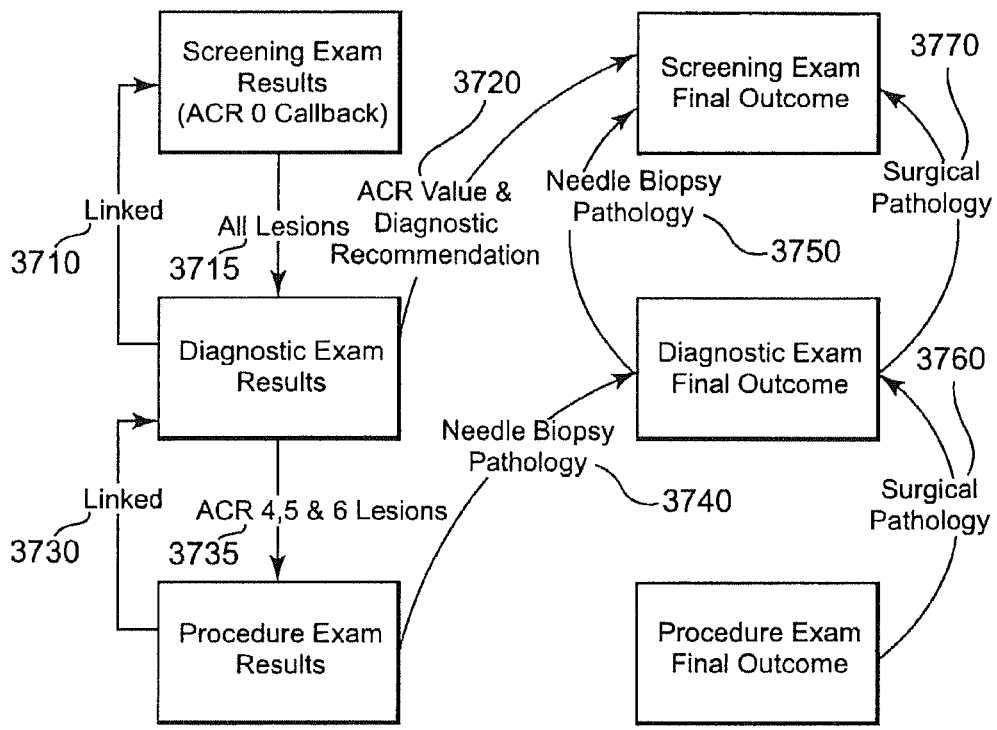
FIG. 37 is a flow diagram that describes steps in a method of data exchange in accordance with one described embodiment.
FIG. 38 is a diagram of an exemplary user interface for a MQSA audit screen in accordance with one specific implementation.

In addition to storing pertinent information of the exams, the mammography management system also provides for data exchanges of the lesions, results and final outcome for a logically linked series of exams, as seen in FIG. 37. For example, a diagnostic exam that is linked (3710) to a screening exam (ACR 0, callback) automatically inherits (3715) through the mammography management system all lesion results from the screening exam. The lesion ACR value and diagnostic recommendation from the diagnostic exam are also automatically fed back (3720) to the screening exam final outcome to populate the same.

Similarly, a procedure exam that is linked (3730) to a diagnostic exam automatically inherits (3735) through the mammography management system any lesion results from the diagnostic exam that have values ACR 4, 5 or 6. The needle biopsy pathology from the procedure exam results and the surgical pathology from the procedure exam final outcome are automatically fed back (3710) to the diagnostic exam final outcome and to the screening exam final outcome 3750 if the link exists to populate the same.

Thus, the screening final outcome is automatically populated 3770 based on results from a subsequent diagnostic exam, and the diagnostic final outcome is automatically populated 3760 based on results from a procedure exam. This linking and automatic data exchange and population facilitates information transfer and related efficiencies of the mammography management system.

Moreover, when the ACR value and diagnostic recommendations are populated from a diagnostic exam result to a screening exam final outcome, the "source of diagnostic recommendation" is set to "mammography management system," and the generated exam report for the diagnostic exam is attached to the diagnostic report field of the screening exam final outcome. Similarly, when a needle biopsy pathology is populated into a diagnostic or screening exam final outcome from the procedure exam result, the "source of needle biopsy pathology" is set to "mammography management system" and the generated exam report for the procedure exam is attached to the needle biopsy report field of the diagnostic/screening exam final outcome. Likewise, when a surgical pathology is populated from a procedure exam final outcome to a diagnostic or screening exam final outcome, the "source of surgical pathology" is set to the same value, and the generated exam report for the procedure exam is attached to the surgical pathology report field of the diagnostic/screening exam final outcome.

Whenever final outcome information is automatically populated to a linked exam, the mammography management system creates an entry in the exam's audit log for the exam that is on the receiving end of the final outcome data population.

Studies

When exams have multiple studies, the mammography management system breaks out the studies into separate tables. This is pertinent to both diagnostic exams, which often have multiple related studies, and screening exams, which only have multiple studies in the case of a "compare" or "tech repeat" result.

When the mammography management system links an incoming study from the PACS system to a diagnostic exam in the mammography management system, the mammography management system matches various fields such as patient name, patient date of birth, and patient MRN. If a match is made and the patient is associated with an active diagnostic exam created on the same day as the study was recorded then the study is linked with the patient and diagnostic exam within the mammography management system.

System Administration

The mammography management system provides for a flexible role-based security model, which complies with HIPAA requirements. The system provides for screen access, which protects each specific screen as desired, functional access, which protects links or other page functions, and data access, which protects stored data.

Every screen in the mammography management system is protected by a specific permission. Each action that can be performed on a data element will also be protected by a specific permission. A user must have the required permission to gain access to the mammography management system screens and certain functions within the screens.

Roles can be created, which include a combination of specific permissions, and then assigned to the desired users. These roles can be managed (created, modified, and deleted) via the mammography management system interface. In order to grant permissions to a user, one or more roles will be assigned to a single user.

Similarly, the mammography management system includes user management screens that allow system users to be added with appropriate role-association and managed by an administrator. The system also includes "add and modify facility" screens that allow a system administrator to add new facilities or modify the details of an existing facility. The system administrator may also user the mammography management system interface to maintain the details of all remote devices that are in use at facilities (including home offices), which connect to and use the mammography management system service. Further, the system administrator may maintain through the mammography management system interface a list of vendors and models associated with the vendors.

MQSA Audit

The Mammography Quality Standards Act (MQSA) requires that mammography facilities meet uniform quality standards, which are intended to lead to early treatment, a range of treatment options, and increased chances of survival. Under the MQSA, all mammography facilities must be accredited by an FDA-approved accreditation body and undergo an annual MQSA audit. The mammography management system facilitates such audits as described herein.

A lead interpreting physician of a facility can generate MQSA audit reports based on various types of filter criteria and comparisons. With reference to FIG. 38, a MQSA audit screen 3800 is shown in accordance with one embodiment of the present invention. The lead interpreting physician or other user may generate reports: by radiologist (compare radiologists to one another), by facility (compare facility to one another), overall, by radiologist/overall (compare radiologist to overall), by radiologist/facility (compare radiologist to facility), by facility/overall (compare facility to overall). The MQSA audit reports include the following result fields: number of screenings, recall rate (percentage of ACR 0a /total number of screenings), biopsy recommended (number of ACR 0's that ended up as ACR-4 or ACR-5), PPV1 (true positives; number of ACR 0's that ended up with a final outcome of cancer, cancers found per 1000 exams read, tumors found (number of stage 0 or 1), tumors found (minimal cancer 1, number <=1 cm), node positivity (number that had nodes), false positives(number of ACR 0's that ended up ACR-1, ACR-2 or ACR-3), false negatives(number of exams marked as negative and a cancer was detected in less than 12 months), sensitivity percentage (PPV1/(PPV1+FNs)* 100), specificity percentage ((TNs)/(FPs+TNs)* 100, where number of true negatives is number of ACR-1's and ACR-2's that were not false negatives), number of lost to follow-up, total number of cancers found during designated period, percentage of cancers that were invasive ductal, percentage of cancers that were DCIS, percentage of cancers that were lobular, percentage of cancers that were of the other types, and percentage of 0's that ended up as high risk(LCIS/ADH/High risk).

As the result of an audit, the lead interpreting physician may mark exams as false negative in the mammography management system when a screening mammogram that was originally rated as an ACR BI-RADS 1 or ACR BI-RADS 2, within 12 months is determined to be cancerous. The facility that performed the diagnostic procedure will inform the screening facility of this occurrence. The lead interpreting physician will be responsible for searching for the exam and marking it as a false negative. Additionally, the mammography management system creates an audit trail throughout normal usage by tracking, storing, and identifying users' access of specific records.

Professional Certifications

Professional certifications functionality provided by the mammography management system allow system users such as radiologist and technologists to track their professional credentials such as licenses, certifications, and education. The functionality is flexible such that a variety of credential types may be entered and stored in the system and so that the progress of such credentials are tracked and monitored for relevant continuing education requirements.

Specifically, the professional certifications functionality of the present invention provides for receiving from a user the user's professional credential including renewal schedule and requirements, such that the renewal requirements are appropriately defined for the credential (such as CEUs). The user may then track progress in the system against the defined renewal requirement by entering specific instances of credit. The user may select to receive from the system reminder emails when his or her credential is due to expire. Further, a user may request from the system a display of all of the user's credentials. A user may also grant permission to other users to view upcoming renewals for all users associated with a facility.

Quality Control

The mammography management system of the present invention provides for quality control of devices associated with the system, such as modalities, monitors used in the radiologists' review station, and printers. The Quality Control (QC) module of the system defines and executes QC tests for medical devices, and includes the ability to configure test plans for specific device types, scheduling of QC tests, data entry of QC test information and the ability to generate several types of QC reports.

Specifically, the quality control functionality allows for an administrator or other user of the system to create a specific QC Test Plan for a Vendor/Model combination, and may include a series of tests to be performed on a designated resource to ensure that the resource is functioning correctly. A Vendor/Model combination (type of device) may have a single QC Test Plan, which is a collection of QC Tests, each with an occurrence. A QC Test may include a check that the test was performed, or it may include a worksheet for data collection. A worksheet contains one or more fields, which may be simple data entries or formula calculations. A calculation formula typically includes two operands and an operator. The operand is either a constant value such as "50" or a reference to the value of another field on the same worksheet. The QC Worksheet screen allows specific data fields to be captured based on the configuration for the QC test. See FIG. 40. Pressing the save button will validate the field and save the data.

Figure 41:
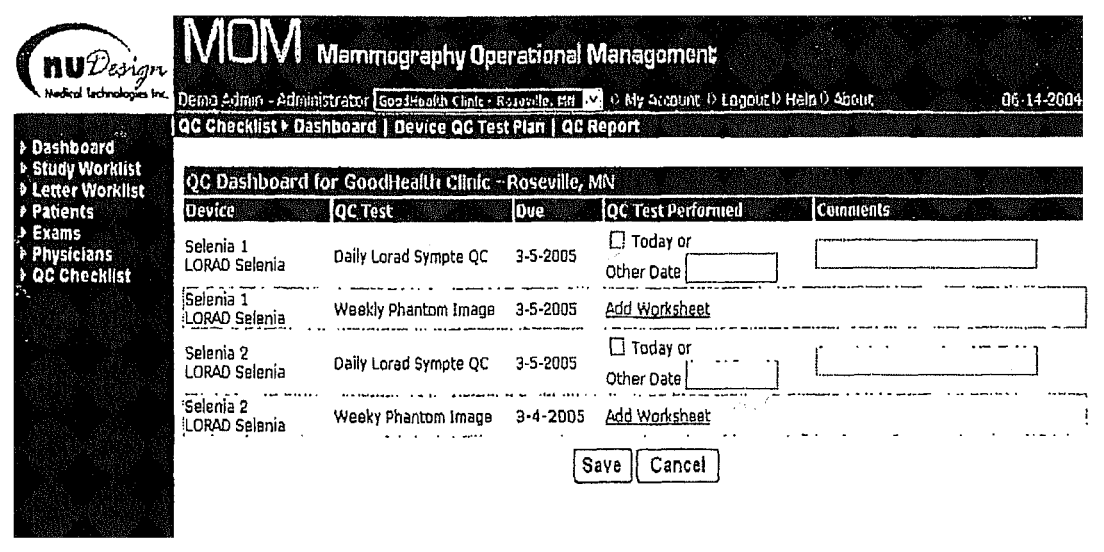

The QC Test Dashboard provides a single screen where all due QC Tests for a facility can be easily viewed and recorded (FIG. 41). The QC Dashboard lists all devices that have a QC Test due today or from a previous day which have not yet been completed. A QC Test that does not require a worksheet will allow the user to select a Today checkbox if they performed the test today, or optional entry of a different date. A QC Test that requires a Worksheet will provide a link to the Worksheet. Clicking the Worksheet link will open the QC Worksheet screen in a popup.

Figure 39:
FIG. 39 is a diagram of an exemplary user interface for a QC test plan setup screen in accordance with one specific implementation.

In order to record QC Test results, the mammography management system is configured for each vendor/model that is to be tracked. A vendor/model has a specific QC Test Plan in the system that contains one or more QC Tests that occur at different intervals. Each test may be a simple as indicating it was completed, or may also include user-defined data fields that to record the various test metrics. The QC test plan setup screen shown in FIG. 39 allows a series of QC Tests to be defined for a specified vendor/model. The QC test plan is then applied to all devices matching the specified vendor/model connected to the mammography management system.

The QC module further provides the ability to define and generate graph reports that convey the requested fields. To define a report, a selects a vendor, which causes the vendor's model listbox to populate with the defined models for the selected vendor. When the user selects a vendor, the system will then populate the worksheet listbox with all of the worksheets that are defined for the vendor/model test plan. The user then selects the desired worksheet from the worksheet listbox and presses a load button, which causes a graph report section to be displayed which allows the user to select report options and fields to graph.

Although various representative embodiments of this invention have been described above with a certain degree of particularity, those skilled in the art could make numerous alterations to the disclosed embodiments without departing from the spirit or scope of the inventive subject matter set forth in the specification and claims.

What is claimed is:

1. A method implemented by a computer system for monitoring medical imaging quality standards, the method comprising:

completing a plurality of worksheet data files, which are selected by a user from a preprogrammed set of worksheet data files templates corresponding to distinct types of quality control tests, with quality control data obtained by running a plurality of quality control tests on one or more medical imaging devices, wherein the one or more medical imaging devices comprises a mammography imaging device, an FFDM imaging device, an MRI imaging device, an X-ray imaging device, or an ultrasound imaging device, wherein a quality control test relates to whether a medical imaging device is functioning correctly and comprises a signal-to-noise quality control test, a contrast-to-noise quality control test, an artifact evaluation quality control test, a detector flat-field calibration quality control test, a phantom image quality control test, a softcopy workstation quality control test or a softcopy workstation quality level quality control test; and wherein the completing of each worksheet data file comprises automatically generating a worksheet data file corresponding to a quality control test run on a medical imaging device;

wherein the worksheet data file is configured with preselected data fields defining at least test metrics based upon the specific medical imaging device type, the date the quality control test was run, an identifier for the medical imaging device, and the identity of the quality control test, and automatically populating values in at least some of the preselected data fields and wherein the generating the worksheet comprises displaying on a screen a graphical representation of the worksheet data file corresponding to the selected template and corresponding test as well as an input button that can be actuated to confirm completion of the worksheet data file within the database and corresponding storage of the completed worksheet and;

maintaining a database comprising a plurality of completed worksheet data files; and generating a report of information collected in at least some of the plurality of worksheet data files contained in the database.

2. The method of claim 1:

wherein a plurality of reports are generated; and wherein the reports are accessible by designated authorized users through a web portal.

3. The method of claim 1 wherein at least one of the preselected data fields comprises a preprogrammed data field selected by a user for collecting information.

4. The method of claim 1 wherein the information in the report is defined by a user selecting preprogrammed criteria.

5. The method of claim 1 wherein the generated report comprises a graph.

6. The method of claim 1 wherein the information in the report comprises results of the quality control tests for determining whether the medical imaging device is functioning properly.

7. The method of claim 1 wherein a quality control test plan specifies a schedule for running the at least some of the quality control tests on at least one medical imaging device.

8. The method of claim 7 wherein the quality control test plan specifies that the at least some of the plurality of quality control tests are run periodically.

9. The method of claim 8, wherein the occurrence frequencies comprises daily, weekly, bi-weekly, monthly, quarterly, semi-annually, and annually.

10. The method of claim 1, wherein some of the information entered in the preselected data fields on the performance of the medical imaging device is received from a testing device for measuring the performance of the medical imaging device.

11. The method of claim 1, wherein the quality control test plan directs the performance of a quality control test on the medical imaging device to generate data received by a worksheet.

12. The method of claim 1, wherein the report is based on comparing a test value to a medical imaging device standard for a pass/fail status, and wherein the test value is derived from performing calculations on data received from performing a quality control test of the quality control test plan on the medical imaging device.

13. A computer system comprising a processor, memory and a program that implements the method of claim 1 on the processor.

14. The method of claim 1, wherein the report is generated for conducting an audit.

15. The method of claim 1 wherein the entering of values in at least some of the preselected data fields comprises the user entering values in at least some of the preselected data fields.

16. The method of claim 1 wherein the test metrics comprise a signal-to-noise and/or contrast-to-noise values.

17. The method of claim 1 wherein the test metrics comprise artifact evaluation data, phantom image data or detector flat-field calibration data.

* * * * *